US009416210B2

(12) United States Patent
Emrick et al.

(10) Patent No.: US 9,416,210 B2
(45) Date of Patent: Aug. 16, 2016

(54) ZWITTERIONIC POLYMERS WITH THERAPEUTIC MOIETIES

(75) Inventors: Todd Emrick, South Deerfield, MA (US); Xiangji Chen, Amherst, MA (US); Samantha McRae, Belchertown, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 488 days.

(21) Appl. No.: 13/131,665

(22) PCT Filed: Dec. 11, 2009

(86) PCT No.: PCT/US2009/067665
§ 371 (c)(1),
(2), (4) Date: Sep. 13, 2011

(87) PCT Pub. No.: WO2010/068862
PCT Pub. Date: Jun. 17, 2010

(65) Prior Publication Data
US 2011/0319569 A1    Dec. 29, 2011

Related U.S. Application Data

(60) Provisional application No. 61/122,065, filed on Dec. 12, 2008, provisional application No. 61/233,982, filed on Aug. 14, 2009.

(51) Int. Cl.
| | | |
|---|---|---|
| *C08F 230/02* | (2006.01) | |
| *C08F 238/00* | (2006.01) | |
| *A61K 47/32* | (2006.01) | |
| *A61K 47/48* | (2006.01) | |
| *C08F 8/30* | (2006.01) | |
| *C08F 220/34* | (2006.01) | |
| *C08F 293/00* | (2006.01) | |

(52) U.S. Cl.
CPC .......... *C08F 230/02* (2013.01); *A61K 47/48176* (2013.01); *C08F 8/30* (2013.01); *C08F 220/34* (2013.01); *C08F 293/005* (2013.01); *C08F 238/00* (2013.01); *C08F 2438/01* (2013.01)

(58) Field of Classification Search
CPC .... C08F 230/02; C08F 228/02; C08F 238/00; C08F 220/28; C08F 220/34; C08F 2438/01; C08F 2220/387; A61K 47/48176; A61K 47/48023

USPC .................. 526/277, 285, 287, 288, 312, 319
See application file for complete search history.

(56) References Cited

U.S. PATENT DOCUMENTS

| | | | | |
|---|---|---|---|---|
| 6,225,431 | B1 * | 5/2001 | Bowers et al. | 526/287 |
| 6,841,639 | B1 * | 1/2005 | Redman et al. | 526/277 |
| 2005/0159556 | A1 * | 7/2005 | Lewis et al. | 525/280 |
| 2006/0165804 | A1 | 7/2006 | Lewis et al. | |
| 2007/0244265 | A1 * | 10/2007 | Matyjaszewski et al. | 525/376 |

FOREIGN PATENT DOCUMENTS

WO      WO 01/09208 A1     2/2001

OTHER PUBLICATIONS

Licciardi et al., Biomacromolecules 6 (2005) 1085-1096.*
Supp. European Search Report (dated May 31, 2012), European Appl. No. EP 09832608.5.
Int'l Search Report (dated Jul. 27, 2010), PCT/US09/067665.
Written Opinion of ISA (dated Jul. 27, 2010), PCT/US09/067665.
Golas et al. "Click Chemistry and ATRP: A Beneficial Union for the Preparation of Functional Materials", QSAR & Combinatorial Science, vol. 26, No. 11-12, pp. 1116-1134 (Dec. 1, 2007).
Chen et al. "Polymeric Phosphorylcholine-Camptothecin Conjugates Prepared by Controlled Free Radical Polymerization and Click Chemistry", Bioconjugate Chemistry, vol. 20, No. 12, pp. 2331-2341 (Dec. 16, 2009).
Lutz et al. "Combining ATRP and "Click" Chemistry: a Promising Platform toward Functional Biocompatible Polymers and Polymer Bioconjugates", Macromolecules, vol. 39, No. 19, pp. 6376-6383 (Sep. 1, 2006).

* cited by examiner

*Primary Examiner* — Roberto Rabago
(74) *Attorney, Agent, or Firm* — Cantor Colburn LLP

(57) ABSTRACT

The invention generally relates to zwitterionic polymers (including zwitterionic copolymers), such as polymethacrylic structures, with pendent functional moieties, such as therapeutic or biologic moieties. More particularly, the invention relates to phosphorylcholine-substituted methacrylic polymers prepared by free radical polymerization and click chemistry, for example, and compositions and products comprising same, as well as related methods and uses of the compositions, for example, as biological or therapeutic agents and in drug delivery thereof.

5 Claims, 21 Drawing Sheets

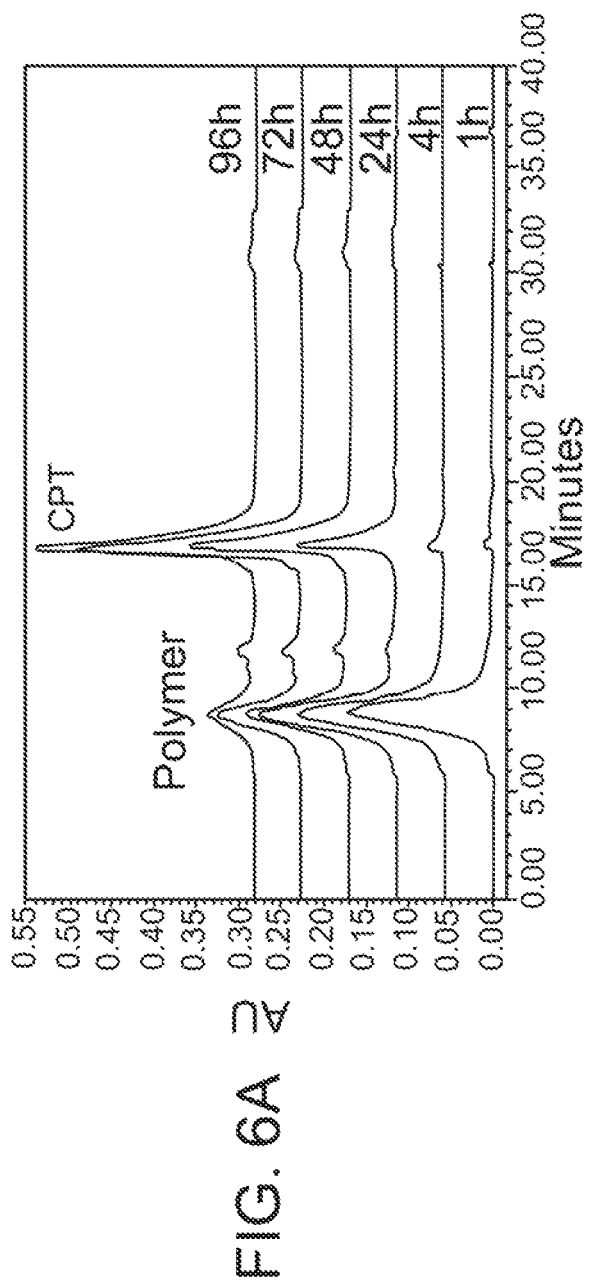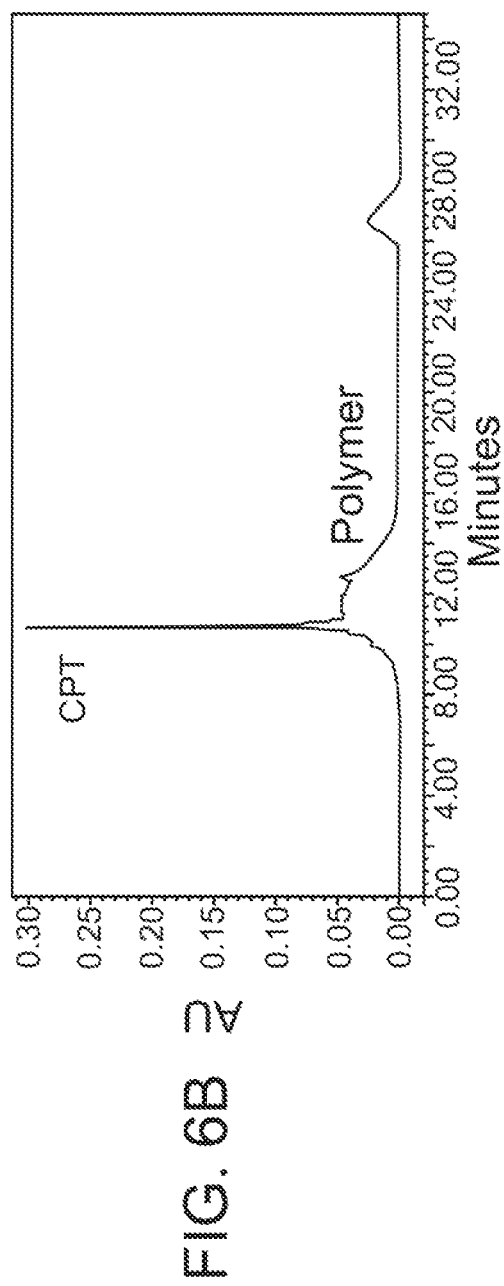
FIG. 6A
FIG. 6B

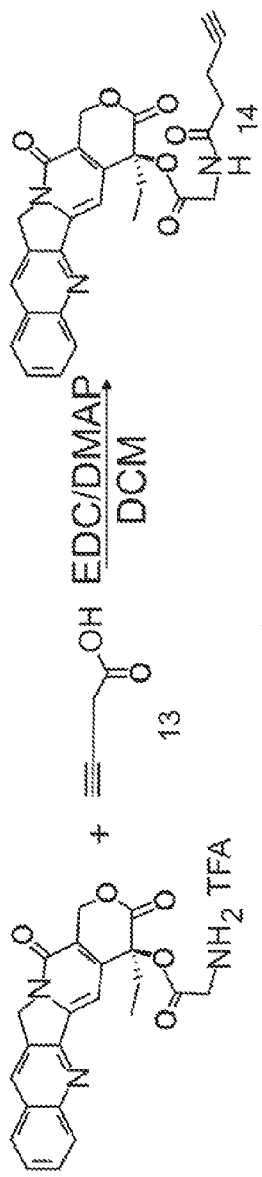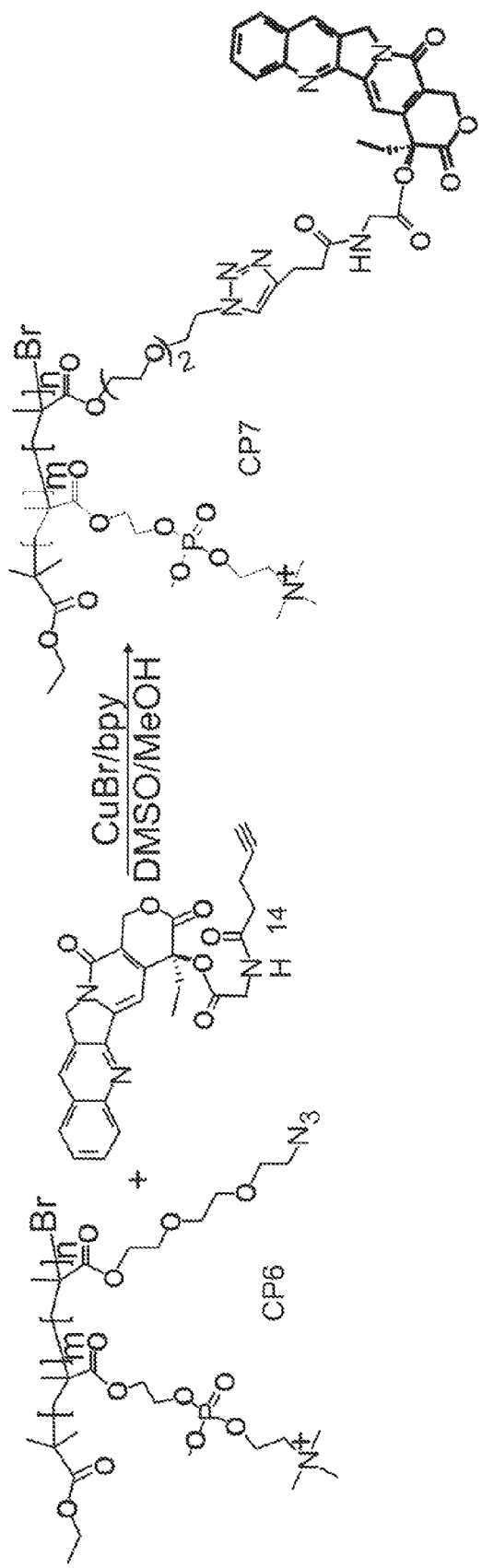
FIG. 14A
FIG. 14B

ZWITTERIONIC POLYMERS WITH THERAPEUTIC MOIETIES

PRIORITY CLAIMS AND RELATED APPLICATIONS

This application claims the benefit of U.S. Provisional Application Nos. 61/122,065 filed Dec. 12, 2008, and 61/233,982 filed Aug. 14, 2009, the entire content of each of which is expressly incorporated herein by reference.

GOVERNMENT RIGHTS

The United States Government has certain rights to the invention pursuant to Grant No. CTS-0553957 from the National Science Foundation to the University of Massachusetts.

FIELD OF THE INVENTION

The invention generally relates to zwitterionic polymers (including zwitterionic copolymers), such as polymethacrylic structures, with pendent functional moieties, such as therapeutic or biologic moieties. More particularly, the invention relates to phosphorylcholine-substituted methacrylic polymers prepared by atom transfer radical polymerization and click chemistry, for example, and compositions and products comprising same, as well as related methods and uses of the compositions, for example, as biological or therapeutic agents and in drug delivery thereof.

BACKGROUND OF THE INVENTION

Small molecule anti-tumor agents used clinically often display poor pharmacokinetics, undesired toxicity and side-effects, and poor water solubility that present delivery difficulties. Numerous chemotherapeutic drugs used today have a relatively low therapeutic index, or therapeutic ratio, described as the lethal dose divided by the therapeutic dose ($LD_{50}/ED_{50}$). In essence, therapeutic benefits are often substantially offset by detrimental side effects.

Conjugation of chemotherapeutics to water-soluble polymers could greatly enhance their aqueous solubility as well as ease of administration, and further reduce side effects towards improving therapeutic efficacy by altering pharmacokinetics. The underlying in vivo characteristics of polymer drugs that lead to their beneficial effects are described by the enhanced permeation and retention (EPR) effect, which provides for a passive and selective uptake of the polymer-bound drugs into tumor tissue, and retention in that tissue due to a characteristic poor lymphatic drainage. (Maeda, et al. *J. Control. Release* 2000, 65 (1-2), 271-284.)

Effective polymer therapeutics require the use of biocompatible polymers with high water solubility and biocompatibility. Poly(ethylene glycol) (PEG) has been conjugated to various therapeutic protein and peptide drugs to enhance their therapeutic efficacy, such as erythropoietin (EPO), granulocyte colony stimulating factor (G-CSF), and interferon (IFN). PEGylation increases the apparent size of the proteins and peptides (thereby reducing the rate of renal clearance), shields them from proteolytic enzymes, and improves their pharmacokinetic profile. (Harris, et al. *Nat. Rev. Drug Discov.* 2003, 2 (3), 214-221.) The advantages stemming from PEGylation led to the development of novel and effective medicines, such as PEG-Intron® (PEGylated Interferon alpha-2b) and Pegasys® (PEGylated Interferon alpha-2a) for the treatment of Hepatitis C. (Veronese, et al. *Drug Discov. Today* 2005, 10 (21), 1451-1458.)

PEGylation has also been used to improve small molecule drug delivery, for example, in chemotherapy. Among PEGylated cancer drug candidates is camptothecin, for which PEGylated versions show modestly enhanced circulation time and reduced side effects. (Greenwald, et al. *Bioorg. Med. Chem.* 1998, 6 (5), 551-562.) PEGylated camptothecin, reported by Enzon, Inc. as Prothecan®, consists of a 40,000 g/mol PEG chain with camptothecin at each chain-end, connected by ester linkages at the C-20-OH position of the drug. Another chemotherapeutic agent, doxorubicin (DOX), has also been improved by PEGylation, including by linear PEG conjugation, for example, as well as through sophisticated architectures such as "bow-tie" dendrimers, with the resulting DOX-polymer therapeutic displaying increased water solubility, decreased toxicity, and enhanced specificity due to the action of the EPR effect. (Rodrigues, et al. *Bioorg. Med. Chem.* 1999, 7 (11), 2517-2524; Lee, et al. *Proc. Natl. Acad. Sci. U.S.A.* 2006, 103 (45), 16649-16654.)

Novel polymer-drug conjugates and methodologies for effective polymer conjugation, however, continue to be a critical unmet need and are strongly desired for improving human health through more effective treatment of cancer and other diseases.

SUMMARY OF THE INVENTION

The invention is based in part on the unexpected discovery of certain novel zwitterionic polymers, and compositions and methods thereof, and their unique and desirable properties. These unique zwitterionic polymers, including co-polymers, have pendent biological or therapeutic moieties. Such polymers, methods for their syntheses, and uses thereof have been discovered to have broad, unexpected applications such as in the fields of materials, diagnostics, therapeutics and drug delivery.

For example, polyMPC copolymers are tailored for Cu(I)-catalyzed Huisgen 1,3-cycloaddition of azides and alkynes. (cf. Kolb, et al. *Angew. Chem.-Int. Edit.* 2001, 40 (11), 2004-2021; Rostovtsev, et al. *Angew. Chem.-Int. Edit.* 2002, 41 (14), 2596-2599; Tornoe, et al. *J. Org. Chem.* 2002, 67 (9), 3057-3064; Wu, et al. *Angew. Chem.-Int. Edit.* 2004, 43 (30), 3928-3932; Helms, et al. *J. Am. Chem. Soc.* 2004, 126 (46), 15020-15021; Parrish, et al. *Bioconjugate Chem.* 2007, 18 (1), 263-267.)

The efficiency and regioselectivity of the azide-alkyne click reaction, combined with its tolerance towards a diverse range of functionality, has enabled the preparation of new and complex materials. (Binder, et al. *Macromol. Rapid Commun.* 2007, 28 (1), 15-54; Meldal, et al. *Chem. Rev.* 2008, 108 (8), 2952-3015.) Well-defined functional materials have also been synthesized by combining Cu(I)-catalyzed ATRP with click chemistry, such as star-shaped polystyrene and glycopolymers. (Gao, et al. *Macromolecules* 2006, 39 (15), 4960-4965; Ladmiral, et al. *J. Am. Chem. Soc.* 2006, 128 (14), 4823-4830.)

The invention disclosed herein takes advantages of click chemistry for bioconjugation and polymer therapeutics, including the robust triazole cycloadduct, the tolerance of click reactions to aqueous conditions and many functional groups, and the high yields typically realized in click cycloaddition.

In one aspect, the invention generally relates to a co-polymer comprising the structural unit of:

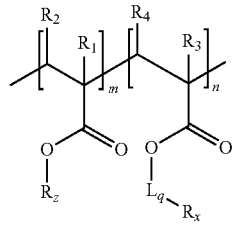

(I)

wherein each of $R_1$ and $R_3$ is independently a hydrogen, alkyl, halogen; each of $R_2$ and $R_4$ is independently a hydrogen, $(C_1\text{-}C_{15})$ alkyl, $(C_1\text{-}C_{15})$ alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; $L_q$ is a linking group (e.g., —$(CH_2)_q$—, wherein q is an integer from about 1 to about 12, e.g., 1, 2, 3, 4, 5, 6); and $R_X$ is a group comprising an azide or a carbon-carbon triple bond (an alkynyl group). In certain embodiments, $R_X$ includes an azide group. In other embodiments, $R_X$ includes a carbon-carbon triple bond. In certain embodiments, the zwitterionic moiety comprises one or more of phosphorylcholine and sulfobetaine.

In another aspect, the invention generally relates to a co-polymer that comprises the structural unit of:

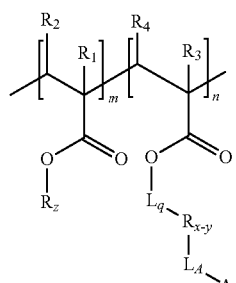

(II)

wherein each of $R_1$ and $R_3$ is independently a hydrogen, alkyl, halogen; each of $R_2$ and $R_4$ is independently a hydrogen, $(C_1\text{-}C_{15})$ alkyl, $(C_1\text{-}C_{15})$ alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; is a linking group (e.g., —$(CH_2)_q$—, wherein q is an integer from about 1 to about 12, e.g., 1, 2, 3, 4, 5, 6); $R_{x\text{-}y}$ is selected from the group consisting of:

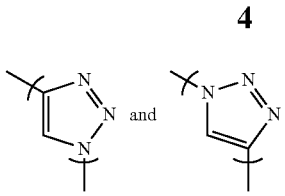

$L_A$ is a linking group; and A is an agent having a biological (e.g., therapeutic or diagnostic) activity. $L_A$, for example, may be a single bond, or a bivalent alkyl, alkyloxy, or aryl group. In some embodiments, A may be a therapeutic agent for treating cancer. For example, A may be selected from campothecin, irinotecin, SN-38, doxorubicin, and derivatives thereof, or other drugs functionalized suitably for click cycloaddition. In some other embodiments, A may be a diagnostic agent.

In yet another aspect, the invention generally relates to a co-polymer that comprises the structure of:

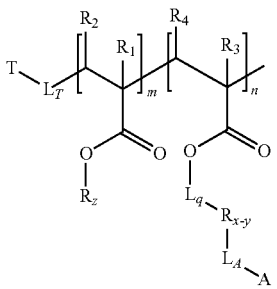

(III)

wherein each of $R_1$ and $R_3$ is independently a hydrogen, alkyl, halogen; each of $R_2$ and $R_4$ is independently a hydrogen, $(C_1\text{-}C_{15})$ alkyl, $(C_1\text{-}C_{15})$ alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; $L_q$ is a linking group (e.g., —$(CH_2)_q$—, wherein q is an integer from about 1 to about 12, e.g., 1, 2, 3, 4, 5, 6); $R_{x\text{-}y}$ is selected from the group consisting of:

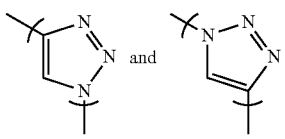

$L_A$ is a linking group; A is an agent having a biological activity; $L_T$ is a linking group; and T is a targeting moiety towards a biological target to which A has biological activity. In certain embodiments, T is selected from the group consisting of: an antibody, protein, aptamer, or a fragment thereof, or a small molecule such as folate. $L_T$, for example, may be an amide group or a group comprising an amide linkage. In some embodiments, A may be a therapeutic agent for treating cancer. For example, A may be selected from campothecin, irinotecin, SN-38, doxorubicin, and derivatives thereof. In some other embodiments, A may be a diagnostic agent.

In yet another aspect, the invention generally relates to a co-polymer that comprises the structure of:

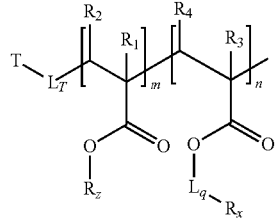

(IV)

wherein each of $R_1$ and $R_3$ is independently a hydrogen, alkyl, halogen; each of $R_2$ and $R_4$ is independently a hydrogen, ($C_1$-$C_{15}$) alkyl, ($C_1$-$C_{15}$) alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; $L_q$ is a linking group (e.g., —($CH_2$)$_q$—, wherein q is an integer from about 1 to about 12, e.g., 1, 2, 3, 4, 5, 6); $R_X$ is a group comprising an azide or a carbon-carbon triple bond; $L_T$ is a linking group; and T is a targeting moiety towards a biological target to which A has biological activity.

In certain embodiments, T is selected from the group consisting of: an antibody, protein, aptamer, or a fragment thereof, or a small molecule such as folate. $L_T$, for example, may be an amide group or a group comprising an amide linkage.

In yet another aspect, the invention generally relates to a co-polymer that comprises the structure of:

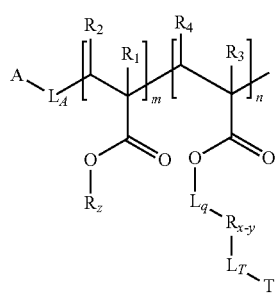

(V)

wherein each of $R_1$ and $R_3$ is independently a hydrogen, alkyl, halogen; each of $R_2$ and $R_4$ is independently a hydrogen, ($C_1$-$C_{15}$) alkyl, ($C_1$-$C_{15}$) alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; $L_q$ is a linking group (e.g., —($CH_2$)$_q$—, wherein q is an integer from about 1 to about 12, e.g., 1, 2, 3, 4, 5, 6); $R_{x-y}$ is selected from the group consisting of:

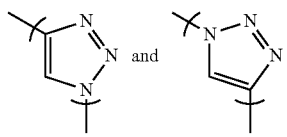

and $L_A$ is a linking group; A is an agent having a biological activity; $L_T$ is a linking group; and T is a targeting moiety towards a biological target to which A has biological activity. In certain embodiments, T is selected from the group consisting of: an antibody, protein, aptamer, or a fragment thereof, or a small molecule such as folate. $L_T$, for example, may be an amide group or a group comprising an amide linkage. In some embodiments, A may be a therapeutic agent for treating cancer. For example, A may be selected from campothecin, irinotecin, SN-38, doxorubicin, and derivatives thereof. In certain embodiments, it may be preferable that m is greater than n. A may also be a diagnostic agent.

Linking groups (e.g., $L_T$, $L_A$, $L_q$) may be any linkage moiety (e.g., a spacer moiety) that serves the purpose of a particular application, for example, may be an alkyl moiety, an amide moiety, an ester moiety, an ether moiety, a hydrazone moiety, or a linkage moiety comprising one of more thereof.

In yet another aspect, the invention generally relates to a polymethacrylate that comprises one or more zwitterion-functionalized pedant groups and one or more biological agent-coupled pedant groups. The ratio of zwitterionic moiety to the biological agent may be from about 2:1 to about 10:1 or greater than 10:1 (e.g., about 3:1, 4:1, 5:1, 6:1, 7:1, 8:1, 9:1, 12:1, 15:1).

In some embodiments, the co-polymers of invention may have a zwitterionic moiety:A ratio from about 2:1 to about 10:1. In certain embodiments, the co-polymers may have a $M_n$ from about 5 kDa to about 200 kDa or greater (e.g., from about 5 kDa to about 100 kDa, from about 5 kDa to about 50 kDa, from about 10 kDa to about 30 kDa, from about 5 kDa to about 100 kDa).

While the preferred embodiments are co-polymers, certain homopolymers (where one of m and n in (I)-(V) is zero) may be useful for certain application.

In certain embodiments, the co-polymer of the invention is cross-linked. Cross-linking can be achieved by any methods known in the art that achieve the desired results.

BRIEF DESCRIPTION OF THE DRAWINGS

FIG. 1A and FIG. 1B together shows an exemplary synthesis of polyMPC-drug conjugates using the drug as an atom transfer radical polymerization (ATRP) initiator and as pendent groups attached by cycloaddition, wherein FIG. 1A shows an acylation step and formation of PolyMPC-drug conjugate and FIG. 1B shows a deprotection step and a click chemistry step to form PolyMPC-CPT/SN-38 conjugate.

FIG. 2 shows exemplary routes to peptide-targeted polymer-drug conjugates.

FIG. 6 shows exemplary (a) SEC-HPLC traces of CP4 incubated with cell culture medium at 37° C. for different times; (b) RP-HPLC trace of CP4 incubated with PBS pH 7.4 for 72 h.

FIG. 14 shows exemplary synthesis of CPT-alkyne compound 14, shown in FIG. 14(a); Conjugation of CPT alkyne compound to azide containing polyMPC with Cu-catalyzed alkyne azide cycloaddition procedure, shown in FIG. 14(b)

DETAILED DESCRIPTION OF THE INVENTION

Figure 1A:
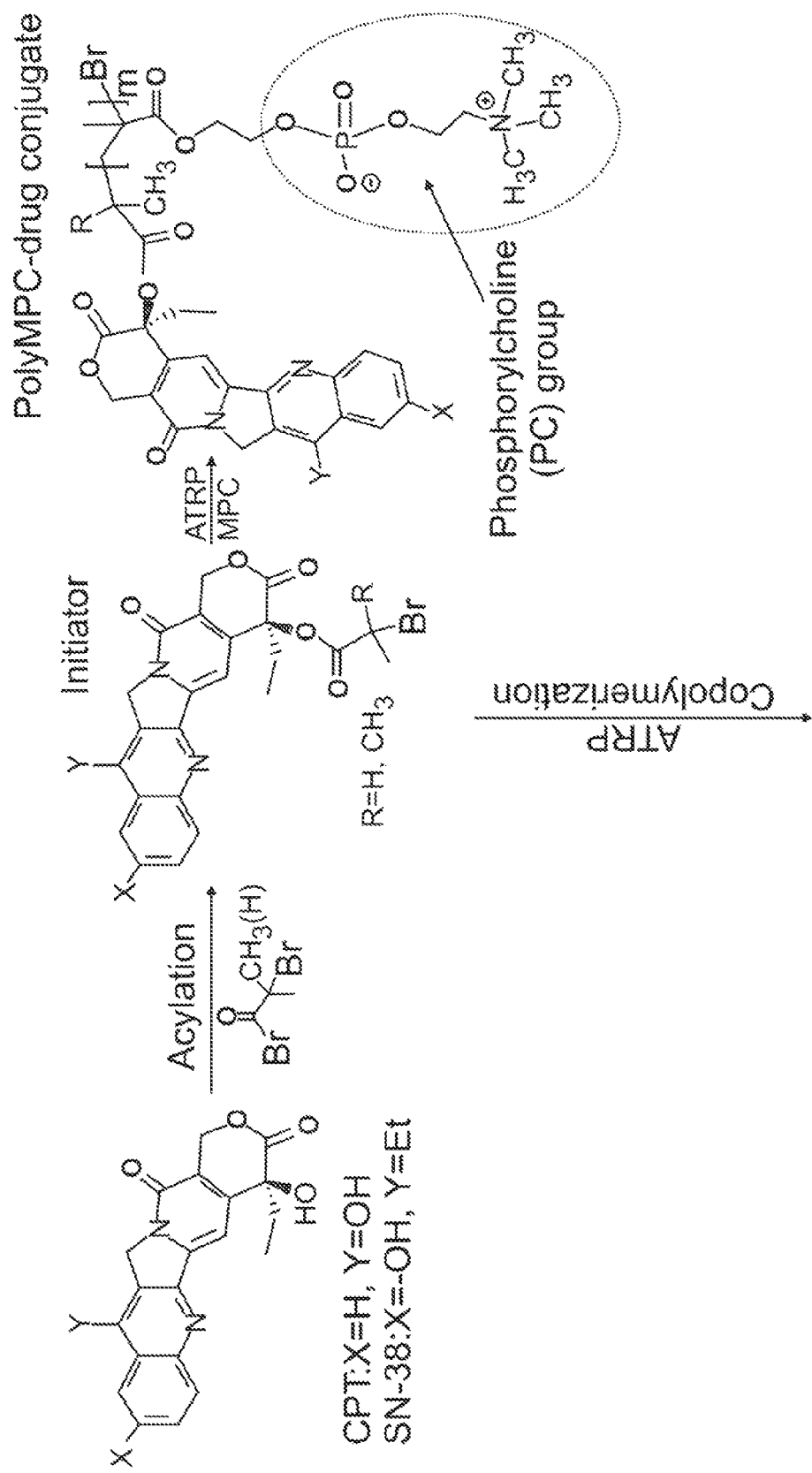

The polymer of the invention, such as phosphorylcholine-substituted methacrylates, i.e., poly(methacryloyloxyethyl phosphorylcholine), and copolymer compositions and methods thereof, have unique and desirable properties and may be useful in various applications such as in materials and in the delivery of therapeutic and diagnostic agents.

Polymer therapeutics, and specifically the use of polymers as carriers for drugs, has shown promise for improving the efficacy of injectable drugs. While the most clinically advanced polymer therapeutics are polymer-modified protein drugs, delivery of small molecule cancer drugs also stands to benefit from polymer conjugation. PEGylation of cancer drugs, via the covalent attachment of poly(ethylene glycol) (PEG) to drug molecules, typically improves their water solubility and dramatically increases their effective size. Improving water solubility of cancer drugs is essential for more effective administration and dosing. Increasing the hydrodynamic radius (or the effective size during circulation) of cancer drugs leads to their longer circulation lifetime in the bloodstream (i.e., less rapid clearance), preferential uptake into the more open vasculature of cancer tissue relative to healthy tissue, and subsequent retention in the cancer tissue due to poor lymphatic drainage. This passive uptake mechanism, described as the enhanced permeation and retention effect (EPR), helps localize chemotherapeutics in cancer tissue, thus limiting deleterious side-effects on healthy tissues. Polymer-functionalized cancer drugs also have advantages of shelf-life and storage (e.g., as dry powders) relative to delivery systems such as liposomal formulations that require solution storage in a certain concentration range and at a certain temperature.

As an example, polymer conjugation as disclosed herein can improve the solubility and drug-loading levels of camptothecin, and camptothecin derivatives such as SN-38, by their covalent attachment to aliphatic polyesters and phosphorylcholine-based polymers. The chosen syntheses provide routes to high drug loading on the polymer backbone, far exceeding reported polymer-camptothecin drug delivery systems. Evaluation of the toxicity of these conjugates relative to the unmodified drugs, by cell culture assays, may provide leads when considering xenograft animal models and biodistribution studies.

Some reported strategies using PEGylated camptothecin permit incorporation of only very few drug molecules per conjugate resulting in low payload and the need for large amounts of injected material for improved treatment outcomes. Polymer-based therapeutics can be designed to increase the drug payload, and to introduce drug cocktails to overcome drug resistance, and also incorporate specialized functionalities such as tissue specific targeting groups. Targeting moieties such as antibodies, small molecules and oligopeptides provide added benefits to therapeutic vehicles by decreasing systemic toxicity and enabling lower dosing for effective treatment.

Phosphorylcholine-containing polymers, such as poly (methacryloyloxyethyl phosphorylcholine) (polyMPC), are known biocompatible polymers. PolyMPC has been used extensively in bulk materials and coatings for contact lenses and blood-contacting devices that require a high level of biocompatibility and resistance to protein adsorption. (Ishihara, et al. *J. Biomater. Appl.* 1998, 13 (2), 111-127; Ishihara, et al. *J. Biomed. Mater. Res.* 1998, 39 (2), 323-330; Ishihara *Front. Med. Biol. Eng.* 2000, 10 (2), 83-95; Lewis *Colloid Surf. B-Biointerfaces* 2000, 18 (3-4), 261-275; Nakabayashi, et al. *Biomaterials* 2003, 24 (13), 2431-2435; Iwasaki, et al. *Anal. Bioanal. Chem.* 2005, 381 (3), 534-546; Ishihara, et al. *J. R. Soc. Interface* 2009, 6, S279-S291.)

As polyMPC has a decidedly lower commercial availability than functional PEG-based derivatives (even the MPC monomer is not readily available), its use in conjugation chemistry towards polymer therapeutics has been limited to only a few examples. PolyMPC has been conjugated to therapeutic proteins, such as erythropoeiten (EPO) and granulocyte-colony stimulating factor (G-CSF), using end-functional derivatives prepared by atom transfer radical polymerization (ATRP). (Samanta, et al. *Biomacromolecules* 2008, 9 (10), 2891-2897.) These structures were shown to possess in vivo pharmacokinetic profiles superior to PEGylated proteins. (Lewis, et al. *Bioconjugate Chem.* 2008, 19 (11), 2144-2155.) Living atom transfer radical polymerization techniques, such as ATRP and RAFT, can enable the preparation of well-defined polyMPC-drug conjugates with diverse architectures that cannot be achieved by conventional PEGylation techniques. (Lobb, et al. *J. Am. Chem. Soc.* 2001, 123 (32), 7913-7914; Ma, et al. *Macromolecules* 2002, 35 (25), 9306-9314; Ma, et al. *Macromolecules* 2003, 36 (10), 3475-3484; Licciardi, et al. *Biomacromolecules* 2005, 6 (2), 1085-1096; Yusa, et al. *Biomacromolecules* 2005, 6 (2), 663-670; Yu, et al. *Biomacromolecules* 2009, 10 (4), 950-958.) In particular, through covalent grafting to polyMPC copolymers, a high drug loading can be envisaged, whereas PEGylation chemistry confines covalent drug attachment to the polymer chain-end(s).

Physical encapsulation of drugs using polyMPC-based micelles has also been reported. MPC copolymers can self-assemble in water to form micelles, and have been prepared to carry drugs sequestered inside the hydrophobic cores. (Licciardi, et al. *Biomacromolecules* 2005, 6 (2), 1085-1096; Yusa, et al. *Biomacromolecules* 2005, 6 (2), 663-670; Yu, et al. *Biomacromolecules* 2009, 10 (4), 950-958; Konno, et al. *J. Biomed. Mater. Res. Part A* 2003, 65A (2), 209-214; Du, et al. *J. Am. Chem. Soc.* 2005, 127 (51), 17982-17983.) An example of the use of micelles for drug delivery is a cholesterol-polyMPC amphiphile that was synthesized and tested as a novel drug delivery system with the therapeutic agent adriamycin (ADR) incorporated into the micelle core. (Xu, et al. *J. Control. Release* 2005, 107 (3), 502-512.) These micelles release drug over the course of several days, and that release was tunable according to polyMPC molecular weight and drug concentration.

Two problems with camptothecin and its derivatives, specifically poor water solubility and structural instability, must be addressed to optimize their use in cancer treatment, and to reduce serious side-effects, such as life-threatening dehydration, associated with their use. As discussed herein, polymers are well-suited for improving water solubility, especially through conjugation methods using biocompatible, water soluble polymers such as poly(ethylene glycol) and phosphorylcholine-based structures. The lactone ring of camptothecin is susceptible to ring-opening under physiological conditions, and the ring-opened form is inactive against tumor cells. Camptothecin derivatives such as SN-38 (hydroxyl group at the 10 position) carry identical problems. Stabilization of the lactone ring of camptothecin derivatives is best accomplished by acylation (ester formation) at the 20-OH position. When acylation is performed with carboxylic acid terminated PEG, a polymer-drug conjugate is obtained that is more soluble and more stable than the drug alone. Such conjugates may contain, for example, one, two, three or four camptothecin molecules per polymer chain. While this chain-end functionalization approach represents state-of-the-art polymer therapeutics for camptothecin derivatives, it cannot address the need for high drug loading, or targeting, desired in an optimized polymer-drug molecule.

The invention generally relates to polymer therapeutics using polymer vehicles with attached drugs that may be used to treat certain conditions, such as certain cancers, and for diagnostic applications. For example, biologically active agents such as camptothecin and SN-38 may be attached to synthetic polymer backbones in ways that can simultaneously impart good drug solubility, high loading levels, structural stability, and targeting on a single polymer chain. The invention may be applied to prepare macromolecules having multiple drugs pendent to the polymer backbone, and surround the drugs by other desired groups (i.e., for solubilization and targeting) in well-defined ratios. The high drug loading resulting from this approach is desired for polymer therapeutics, but could not be achieved by conventional methods, for example by PEGylation.

In one aspect, the invention generally relates to a co-polymer comprising the structure of:

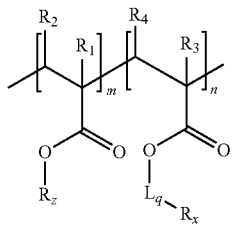

(I)

wherein each of $R_1$ and $R_3$ is independently a hydrogen, an alkyl, halogen; each of $R_2$ and $R_4$ is independently a hydrogen, $(C_1-C_{15})$ alkyl, $(C_1-C_{15})$ alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; $L_q$ is a linking group (e.g., —$(CH_2)_q$—, wherein q is an integer from about 1 to about 12, e.g., 1, 2, 3, 4, 5, 6); and $R_X$ is a group comprising an azide or a carbon-carbon triple bond. In certain embodiments, $R_X$ includes an azide group. In other embodiments, $R_X$ includes a carbon-carbon triple bond. The zwitterionic moiety comprises one or more of phosphorylcholine and sulfobetaine. In certain embodiments, it may be preferable that m is greater than n.

Phosphorylcholine has the structure of

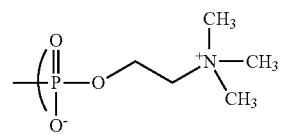

The sulfobetaine has the structure:

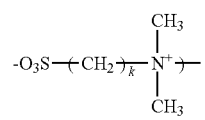

wherein k is an integer from about 1 to about 15.

In another aspect, the invention generally relates to a co-polymer that comprises the structure of:

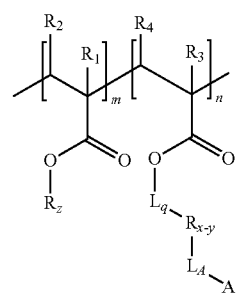

(II)

wherein each of $R_1$ and $R_3$ is independently a hydrogen, alkyl, halogen; each of $R_2$ and $R_4$ is independently a hydrogen, $(C_1-C_{15})$ alkyl, $(C_1-C_{15})$ alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; $L_q$ is a linking group (e.g., —$(CH_2)_q$—, wherein q is an integer from about 1 to about 12, e.g., 1, 2, 3, 4, 5, 6); $R_{x-y}$ is selected from the group consisting of:

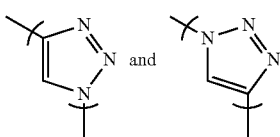

$L_A$ is a linking group; and A is an agent having a biological activity (e.g., a protein, antibody, enzyme, or small molecule or polymeric agent, or fragments thereof). $L_A$, for example, may be a single bond, or a bivalent alkyl, alkyloxy, or aryl group. In some embodiments, A may be a therapeutic agent for treating cancer. For example, A may be selected from campothecin, irinotecin, SN-38, doxorubicin, and derivatives thereof. In certain embodiments, it may be preferable that m is greater than n.

In yet another aspect, the invention generally relates to a co-polymer that comprises the structure of:

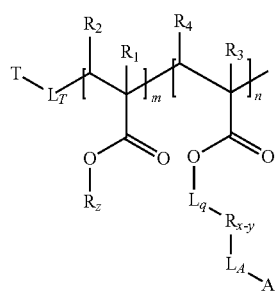

(III)

wherein each of $R_1$ and $R_3$ is independently a hydrogen, alkyl, halogen; each of $R_2$ and $R_4$ is independently a hydrogen, $(C_1-C_{15})$ alkyl, $(C_1-C_{15})$ alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; $L_q$ is a linking group (e.g., $-(CH_2)_q-$, wherein q is an integer from about 1 to about 12, e.g., 1, 2, 3, 4, 5, 6); $R_{x-y}$ is selected from the group consisting of:

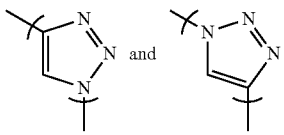

$L_A$ is a linking group; A is an agent having a biological activity; $L_T$ is a linking group; and T is a targeting moiety towards a biological target to which A has biological activity. In certain embodiments, T is selected from the group consisting of: an antibody, protein, aptamer, or a fragment thereof, or a small molecule such as folate. $L_T$, for example, may be an amide group or a group comprising an amide linkage. In some embodiments, A may be a therapeutic agent for treating cancer. For example, A may be selected from campothecin, irinotecin, SN-38, doxorubicin, and derivatives thereof. In certain embodiments, it may be preferable that m is greater than n.

Linking groups (e.g., $L_T$, $L_A$, $L_q$) may be any linkage moiety (e.g., a spacer moiety) that serves the purpose of a particular application, for example, may be an alkyl moiety, an amide moiety, an ester moiety, an ether moiety, or a linkage moiety comprising one of more thereof. For example, a linking group may include a carbonyl, an amino, an amino acid, alkoxy, or combinations thereof.

Polymers of the invention may be random or non-random co-polymers (including statistical) and may be block copolymers. For simplicity of formulae and not limitation, the structural formulae used herein are described as block copolymers. However, the formulae shall be understood to include random copolymers as well as (multiple) block copolymers. In addition, certain formulae (for example, formulae III, IV and V) shall be understood to include copolymers in which the T group (or A group) at the terminal is attached to a monomer containing the $R_z$ group or a monomer containing the A or $R_x$ group (or T group).

In yet another aspect, the invention generally related to a co-polymer comprising the structure of:

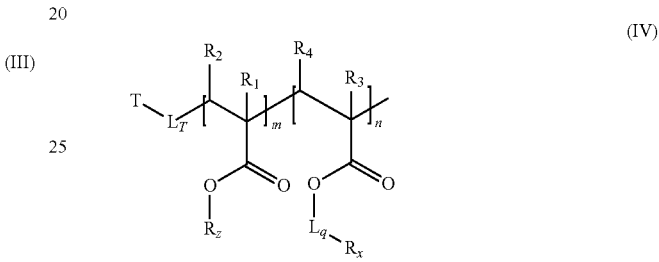

(IV)

wherein each of $R_1$ and $R_3$ is independently a hydrogen, alkyl, halogen; each of $R_2$ and $R_4$ is independently a hydrogen, $(C_1-C_{15})$ alkyl, $(C_1-C_{15})$ alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; $L_q$ is a linking group (e.g., $-(CH_2)_q-$, wherein q is an integer from about 1 to about 12, e.g., 1, 2, 3, 4, 5, 6); $R_X$ is a group comprising an azide or a carbon-carbon triple bond; $L_T$ is a linking group; and T is a targeting moiety towards a biological target to which A has biological activity. In certain embodiments, it may be preferable that m is greater than n.

In certain embodiments, T is selected from the group consisting of: an antibody, protein, aptamer, or a fragment thereof, or a small molecule such as folate. $L_T$, for example, may be an amide group or a group comprising an amide linkage.

In yet another aspect, the invention generally relates to a co-polymer that comprises the structure of:

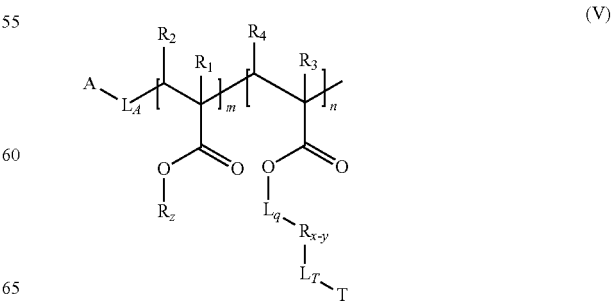

(V)

wherein each of $R_1$ and $R_3$ is independently a hydrogen, alkyl, halogen; each of $R_2$ and $R_4$ is independently a hydrogen, ($C_1$-$C_{15}$) alkyl, ($C_1$-$C_{15}$) alkyloxy, halogen; $R_Z$ is a group comprising a zwitterionic moiety; m is an integer from about 0 to about 500 (e.g., from about 1 to about 500, from about 10 to about 500, 15 to about 300, from about 20 to about 200, from about 25 to about 150); n is an integer from about 0 to about 100 (e.g., from about 1 to about 100, from about 2 to about 50, from about 5 to about 40, from about 10 to about 30), m and n are not both zero; $L_q$ is a linking group (e.g., —(CH$_2$)$_q$—, wherein q is an integer from about 1 to about 12, e.g., 1, 2, 3, 4, 5, 6); $R_{x-y}$ is selected from the group consisting of:

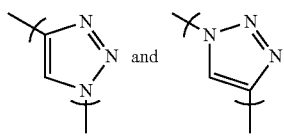

$L_A$ is a linking group; A is an agent having a biological activity; $L_T$ is a linking group; and T is a targeting moiety towards a biological target to which A has biological activity. In certain embodiments, T is selected from the group consisting of: an antibody, protein, aptamer, or a fragment thereof, or a fragment thereof, or a small molecule such as folate. $L_T$, for example, may be an amide group or a group comprising an amide linkage. In some embodiments, A may be a therapeutic agent for treating cancer. For example, A may be selected from campothecin, irinotecin, SN-38, doxorubicin, and derivatives thereof. In certain embodiments, it may be preferable that m is greater than n.

In certain embodiments of the copolymer (I), -$L_q$-$R_x$ may be -($L_q$)$_{n'}$-$R_{x'}$, wherein (n') is zero or 1-10; $L_{q'}$ is a bifunctional linker; $R_{x'}$ is hydrogen, an azide-containing moiety, an alkyne-containing moiety, —$R_{x-y}$-$L_n$-A or —$R_{x-y}$-$L_T$-T; and the other variables are the same as defined above, provided that the copolymer includes one or more groups selected from the group consisting of an azide-containing moiety, an alkyne-containing moiety, and —$R_{x-y}$-$L_a$-A and —$R_{x-y}$-$L_T$-T.

In yet another aspect, the invention generally relates to a polymethacrylate that comprises zwitterion-functionalized pendent groups and biological agent-coupled pendent groups. The ratio of zwitterionic moiety to the biological agent may be from about 2:1 to about 10:1.

In some embodiments, the co-polymers of invention may have a zwitterionic moiety:A ratio from about 2:1 to about 10:1 (e.g., from about 2:1 to about 5:1, from about 5:1 to about 10:1). In certain embodiments, the co-polymers may have a $M_n$ from about 5 kDa to about 200 kDa or greater (e.g., from about 5 kDa to about 100 kDa, from about 5 kDa to about 50 kDa, from about 10 kDa to about 30 kDa).

In certain embodiments, the co-polymer of the invention is cross-linked. Cross-linking may be achieved by any methods known in the art that achieve the desired results.

In one embodiment of the invention, camptothecin and SN-38 are applied to polymer therapeutics or diagnostics in ways that can simultaneously impart drug solubility, loading, stability, and targeting to a single polymer chain. An approach is to have multiple drugs pendent to a polymer chain, which contains other desired groups in well-defined ratios. An azide-modified acylated camptothecin is prepared, and cycloaddition ("click") chemistry is used for its attachment to alkyne-containing polymers. The percentage of alkyne-containing monomer in the polymer structure thus dictates camptothecin loading on the polymer. Upon hydrolysis or enzymolysis, camptothecin cleaves from the backbone in its active lactone form. The principles of polymer therapeutics are expected to localize the drug in the tumor area prior to drug cleavage from the backbone.

The present invention thus enables the preparation of novel highly tailored polymer-drug structures as alternatives to current options in chemotherapy. To this end, the synthetic approach is designed to provide unique structures differentiated from those available commercially, or reported in the literature, but sufficiently simple to envisage scale-up to a production level.

Synthesis of Polymer-Camptothecin and Polymer-SN-38 Conjugates.

Camptothecin/SN-38 Initiators.

20(S)-Camptothecin (CPT), a natural alkaloid, was first isolated from the Chinese tree Camptotheca acuminate in the 1960s. (Wall, et al. *J. Am. Chem. Soc.* 1966, 88 (16), 3888-3890.) CPT shows potent anticancer activity over a broad range of cancer cells, but has poor water solubility and high toxicity that has limited its clinical use. (Slichenmyer, et al. *J. Natl. Cancer Inst.* 1993, 85 (4), 271-291; Muggia, et al. in *Conference on the Camptothecins—From Discovery to the Patient*; Pantazis, P., Giovanella, B. C., Rothenberg, M. L., Eds.; New York Acad Sciences: Bethesda, Md., 1996, p 213-223.) The more water-soluble CPT-derivatives, Topotecan and Irinotecan, were approved in 1997 by the U.S. Food and Drug Administration (FDA) to treat some forms of ovarian and colon cancers. However, like CPT, the efficacy of these derivatives is compromised by ring-opening of the lactone ("E-ring") of these structures to the corresponding carboxylate at physiological pH. (Herben, et al. *Clin. Pharmacokinet.* 1996, 31 (2), 85-102; Mathijssen, et al. *Clin. Cancer Res.* 2001, 7 (8), 2182-2194.) Binding of the carboxylate to serum albumin contributes to drug toxicity. In order to help solubilize CPT, its conjugation to water soluble polymers has been explored, especially by acylation at the 20-OH position; this carries an added benefit of stabilizing the ring-closed form of the drug. (Zhao, et al. *J. Org. Chem.* 2000, 65 (15), 4601-4606.) Water-soluble polymers such as poly(ethylene glycol) (PEG), poly-N-(2-hydroxypropyl)methacrylamide (HPMA), poly-L-glutamic acid (PG), cyclodextrin-based polymers, and PEG-grafted polyesters have been used to conjugate CPT; these polymer-CPT conjugates show increased efficacy over CPT to varying degrees. (Greenwald, R et al. *J. Med. Chem.* 1996, 39 (10), 1938-1940; Zamai, et al. *Mol. Cancer Ther.* 2003, 2 (1), 29-40; Caiolfa, et al. in *9th International Symposium on Recent Advances in Drug Delivery Systems*; Elsevier Science Bv: Salt Lake City, Utah, 1999, p 105-119; Singer, et al. in *International Symposium on Tumor Targeted Delivery Systems*; Elsevier Science Bv: Bethesda, Md., 2000, p 243-247; Zou, et al. *Int. J. Oncol.* 2001, 18 (2), 331-336; Bhatt, et al. *J. Med. Chem.* 2003, 46 (1), 190-193; Cheng, et al. *Bioconjugate Chem.* 2003, 14 (5), 1007-1017; Cheng, et al. *Mol. Pharm.* 2004, 1 (3), 183-193; Parrish, et al. *Bioconjugate Chem.* 2007, 18 (1), 263-267.)

Figure 1B:
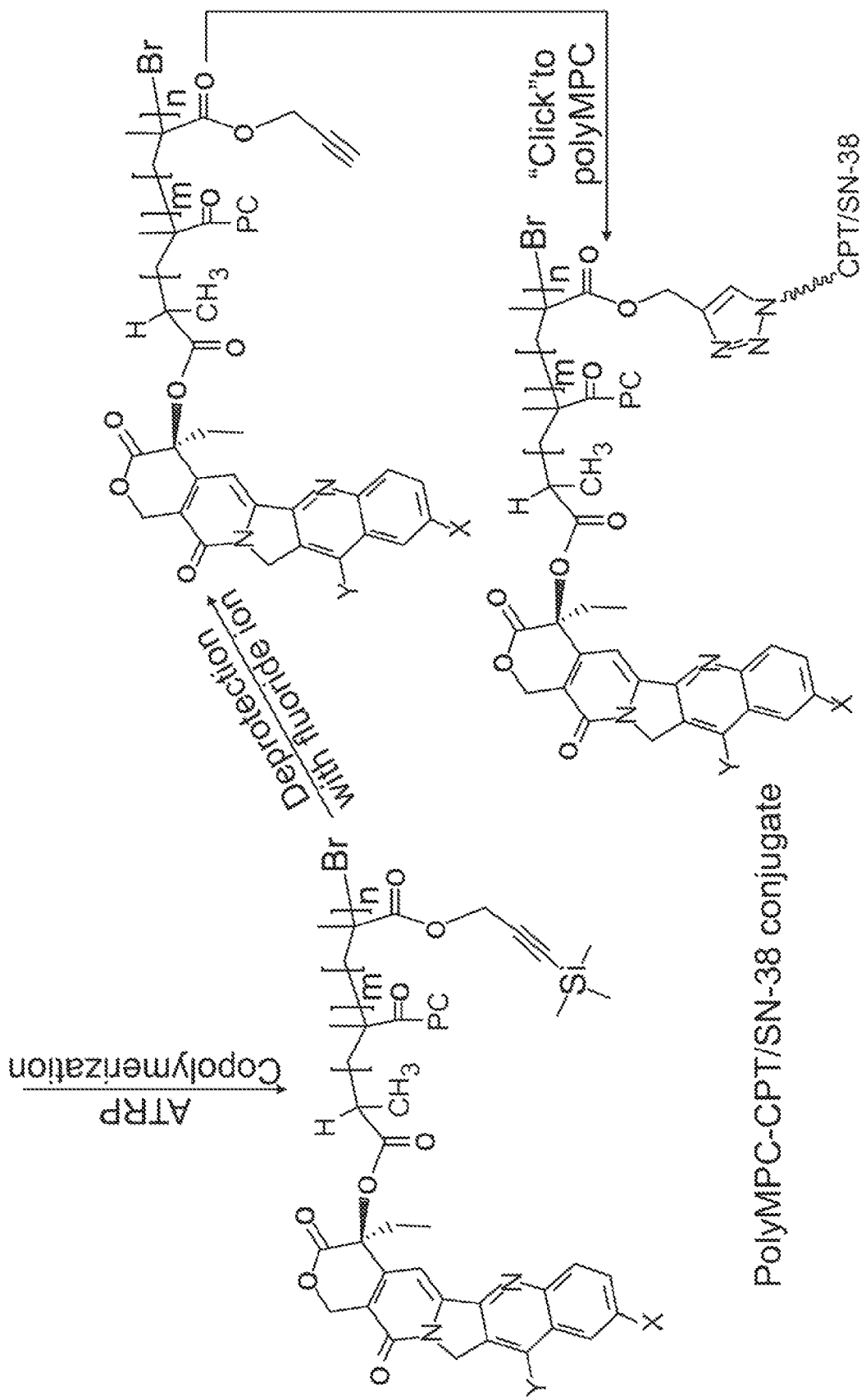
Figure 2A:
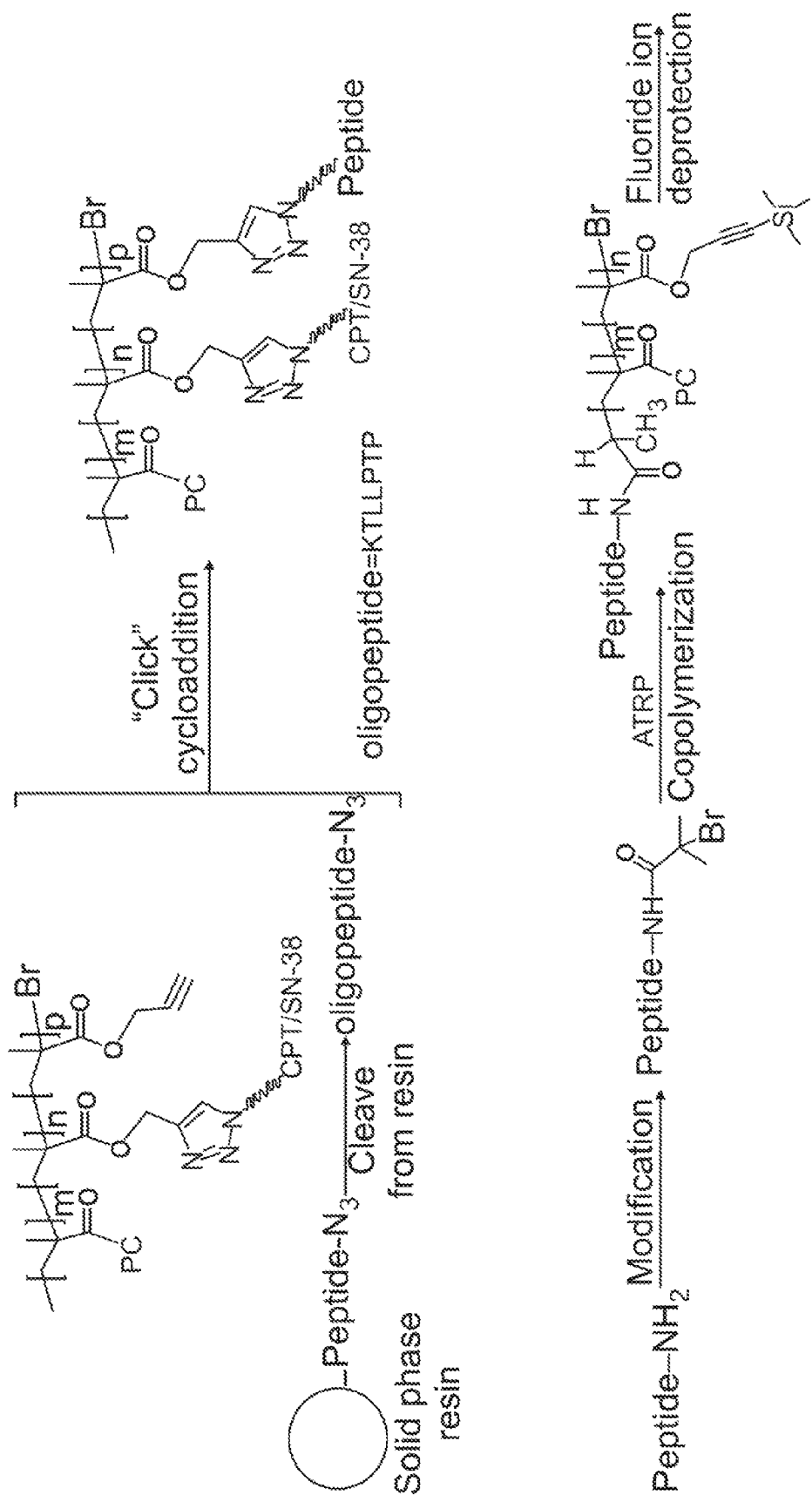
FIG. 2A the oligopeptide-azide is attached to the conjugate by cycloaddition with alkyne groups on the polymer or modified to give an ATRP initiator.
Figure 2B:
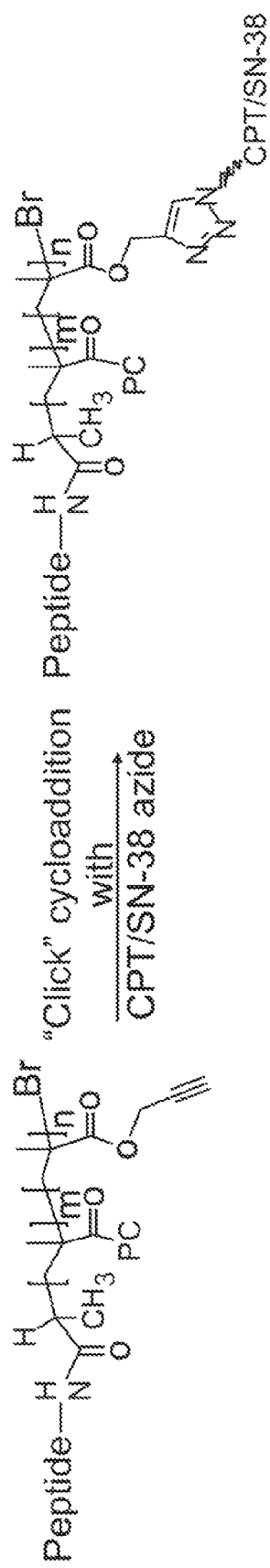
FIG. 2B azide-modified drug is attached to the oligopeptide-terminated polymer by cycloaddition.

FIG. 1 depicts the acylation at the 20-OH position of CPT and SN-38 with 2-bromoisobutyryl bromide or 2-bromopropionyl bromide to give atom transfer radical polymerization (ATRP) initiators for polymerizing MPC. These compounds are suitable initiators for ATRP of MPC, a controlled free radical polymerization that leads to MPC-drug conjugates with low polydispersity, a desirable feature for making well-defined macromolecules that can be considered as injectables for drug delivery. Characterization of MPC-drug conjugates by aqueous gel permeation chromatography (GPC) shows them to be the product of a well controlled polymerization, in which molecular weights from about 5 to about 25 kDa and PDI values of about 1.2 are obtained. Proton NMR spectroscopy of the conjugates indicates the formation of encapsulated drug, by near baseline broadening of the hydrophobic drug peaks in aqueous solvent, and by the appearance of the peaks in polar organic solvents. Critical micelle concentrations of these and other conjugates are measured by light scattering in solution.

MPC with Pendent CPT/SN-38.

While the use of CPT or SN38 to initiate MPC polymerization provides the first examples of MPC-camptothecin/SN-38 conjugates for analysis, these conjugates are restricted to one drug per chain, and higher drug loading is desired. PolyMPC-drug conjugates may be synthesized to afford high drug loadings, by copolymerization of MPC and trimethylsilyl (TMS)-protected propargyl methacrylate from a suitable ATRP initiator (either a conventional initiator or a targeting group derivative). This synthesis is also shown in FIG. 1 (bottom). Following the MPC-alkyne methacrylate copolymerization, the TMS group is removed with tetra-n-butylammonium fluoride, and the liberated alkynes are conjugated to camptothecin/SN-38 azide. The ratio of comonomers used in the initial polymerization dictates the extent of alkyne available for reaction with the azide-labeled drugs.

Drug Release Measurements.

Polymer therapeutic strategies rely on the EPR effect for passive tumor localization; however, their success depends heavily on the efficient release of the drugs from the polymer backbones in the tumor micro-environment and in the cells. Tumors, including pancreatic tumors, harbor an acidic environment (~pH 6.0), necessitating design of pH sensitive polymer-drug conjugates. This reasoning is further supported by the fact that most polymer-drug conjugates post cellular entry get trafficked along the endosomal-lysosomal pathway wherein they are exposed to ~pH 6.5-5.0 in the early and late endosomes to even more acidic regions in the lysosomes.

Time dependent stability of polymer-camptothecin/SN38 conjugates is determined in phosphate buffered saline (PBS), as well as in serum-containing and serum-free cell culture media at different time points. The effect of serum proteins including various esterases on the polymer-drug conjugate stability at physiological pH of 7.4 can then be compared to that in serum-free cell culture medium and in PBS. The Waters Alliance HPLC system connected with a C18 reverse-phase column (250×4.6 mm) is used. Under gradient system of from about 5 to about 95% acetonitrile in 20 min. at a flow rate of 1 mL/min., open-ring and closed-ring camptothecins are well-separated, eluted at retention times of 8.0 and 10.6 min., respectively. The conjugates are dissolved into PBS with different pH values such as pH 7.4 and pH 5.5 to mimic physiological as well as endosomal/lysosomal pH at 37° C. Aliquots are removed at different time intervals, and after addition of an equal amount of dimethyl sulfoxide to dissolve the free drug released from the polymer, the samples are analyzed by HPLC, measuring the drug concentration released from conjugate. The percentage of drug released is calculated on the basis of peak area of the sample at different time points.

Similarly, the polyMPC-drug conjugate is incubated with cell culture media and mouse serum/plasma at 37° C. at different time intervals, and then quenched with a 1:1 mixture of acetonitrile/methanol. After vortexing and passage through a 0.2 μm filter membrane, the samples are analyzed by HPLC. Cell Culture Studies of Polymer-Camptothecin/SN-38 Conjugates.

Cytotoxicity of Polymer-Camptothecin/SN-38 Conjugates.

Preliminary cell-culture experiments were conducted using polyMPC-drug conjugates and PEGylated-polyester-drug conjugates, using weight percent camptothecin on human breast adenocarcinoma cells (MCF7) (American Type Culture Collection, ATCC). Unlike the free drugs, the conjugates prior to release of the drug do not cause any significant cytotoxicity to these cells. This not only demonstrates the biocompatible nature of the polyMPC and PEGylated polyester structures, but also shows that covalent conjugation of the drug to the polymer can mask drug toxicity before its release. Following successful identification of polymer-drug candidates from the hydrolysis studies (see above), cell culture assays may be used to further characterize the conjugates. The human pancreatic cancer cell lines BxPC-3 and AsPC-1 (both from ATCC) are cultured in RPMI-1640 medium supplemented with 10% fetal bovine serum (FBS), and human pancreatic cancer cell line MIA PaCa-2 (ATCC) is cultured in Dulbecco's modified eagle's medium (DMEM) supplemented with 10% FBS and 2.5% horse serum, then incubated at 37° C. At about 70% confluency, the cells are incubated for 24, 48 and 72 hours with varying drug-equivalent concentrations.

This provides valuable data associated with (1) stability of the polymer-drug conjugates as a function of time and (2) the pH-sensitivity of camptothecin/SN38 release. Cell viability post treatment is measured using CellTiter-Glo luminescent cell viability assay (Promega) on a FLUOstar OPTIMA plate reader (BMG LABTECH). The percentage camptothecin or SN38-mediated toxicity is then calculated with respect to untreated cells used as a control sample.

Uses for Treating Cancer

The methods herein are highly relevant to cancer therapy. The ability to tailor polymer structures with high drug loading, water solubility, well-defined solution structures and tissue specific peptides for targeted drug delivery enables design of novel polymer therapeutics for treating various cancer types. The polymer therapeutics approach provides several salient features, including: (1) a large drug payload thereby reducing the therapeutic dose administered to the patient and uptake by both the EPR effect and targeted delivery strategies for cancer cells, (2) the use of biodegradable or biologically inert polymers for the drug conjugation, which can mask the drug during circulation; and (3) a built-in ability to release the attached drug specifically in the tumor microenvironment, as well as intra-cellularly.

Novel Click Chemistry for PolyMPC Copolymers

Described here is the preparation of polyMPC copolymers tailored for Cu(I)-catalyzed Huisgen 1,3-cycloaddition of azides and alkynes. (cf. Kolb, et al. *Angew. Chem.-Int. Edit.* 2001, 40 (11), 2004-2021; Rostovtsev, et al. *Angew. Chem.-Int. Edit* 2002, 41 (14), 2596-2599; Tornoe, et al. *J. Org. Chem.* 2002, 67 (9), 3057-3064; Wu, et al. *Angew. Chem.-Int. Edit.* 2004, 43 (30), 3928-3932; Helms, et al. *J. Am. Chem. Soc.* 2004, 126 (46), 15020-15021; Parrish, et al. *Bioconjugate Chem.* 2007, 18 (1), 263-267.) The efficiency and regioselectivity of the azide-alkyne click reaction, combined with its tolerance towards a diverse range of functionality, has enabled the preparation of new and complex materials. (Binder, et al. *Macromol. Rapid Commun.* 2007, 28 (1), 15-54; Meldal, et al. *Chem. Rev.* 2008, 108 (8), 2952-3015.) Well-defined functional materials have also been synthesized by combining Cu(I)-catalyzed ATRP with click chemistry, such as star-shaped polystyrene and glycopolymers. (Gao, et al. *Macromolecules* 2006, 39 (15), 4960-4965; Ladmiral, et al. *J. Am. Chem. Soc.* 2006, 128 (14), 4823-4830.) Exploited here are the advantages of click chemistry for bioconjugation and polymer therapeutics, including the robust triazole cycloadduct, the tolerance of click reactions to aqueous conditions and many functional groups, and the high yields typically realized in click cycloaddition.

Figure 3A:
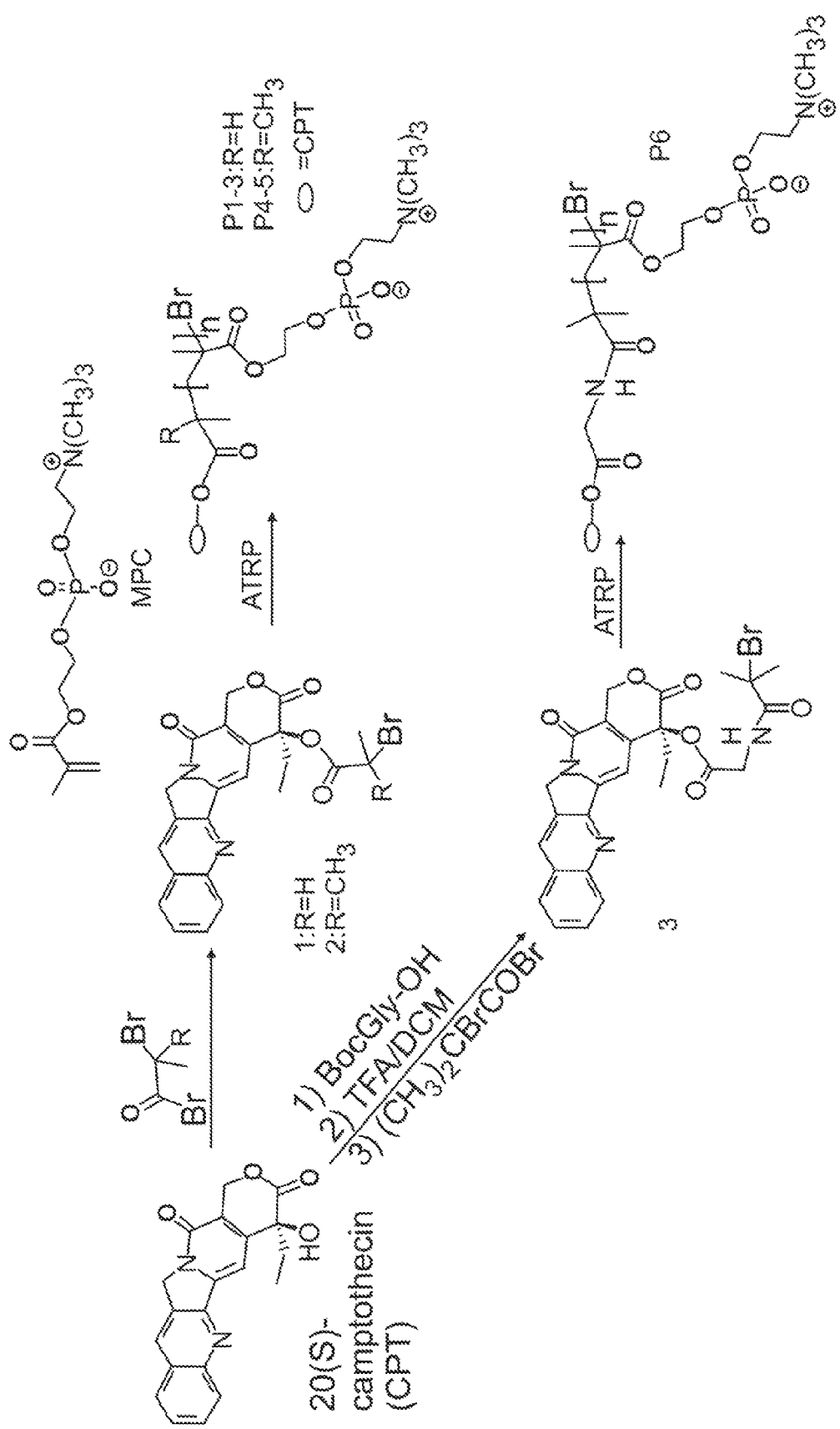
FIG. 3 shows an exemplary (a) synthesis of ATRP initiators (1, 2 and 3) and CPT terminated polyMPC polymers by ATRP and (b) aqueous GPC trace of CPT terminated polyMPC HP2.
Figure 3B:
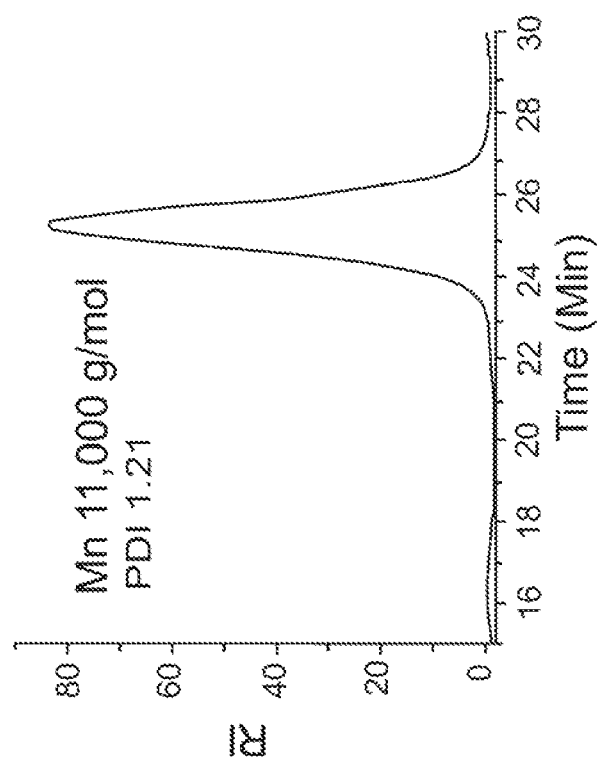
Figure 4A:
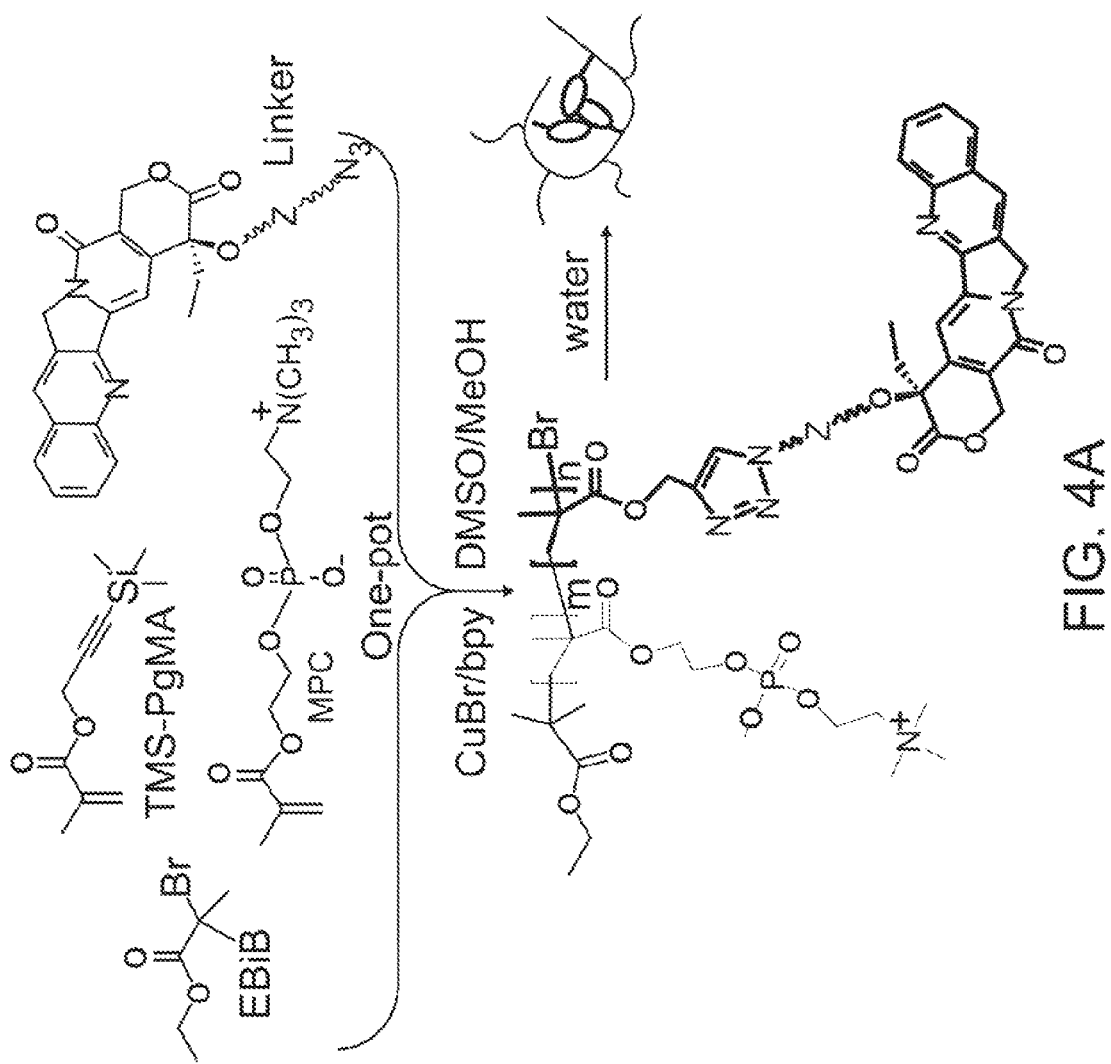
FIG. 4 shows an exemplary (a) one-pot synthesis of CPT-polyMPC conjugates; (b) aqueous GPC trace of copolymer CP5; (c) a plot of light scattering intensity with concentration of CP5 and insert is polymer diameter distribution.

The invention disclosed here enables click chemistry to be applied to the polyMPC backbone, using an acylated and azide-modified CPT, to give polyMPC-CPT conjugates with high drug loading and potential for future integration into CPT-based injectable cancer therapeutics. To first demonstrate the compatibility of CPT with ATRP chemistry, CPT was functionalized with propionyl bromide and isobutyryl bromide, giving CPT-ATRP initiators for polymerization of MPC (FIG. 3). This approach gives CPT-polyMPC conjugates (one drug per chain). Then, polyMPC copolymers were prepared in which CPT is integrated into the structure as pendent groups (FIG. 4). The latter strategy allows control over drug loading, as incorporation of CPT was altered by varying the feed ratio of the alkyne monomer. Different drug release rates were achieved by incorporating different linkers between CPT and the MPC polymer. Lastly, cell culture experiments were performed to test the activity of the conjugates in vitro.

EXAMPLES

Synthesis of CPT-Terminated polyMPC.

CPT-ATRP initiators 1 and 2 were synthesized as shown in FIG. 3. The 20-OH group of CPT was acylated with 2-bromopropionyl bromide and 2-bromoisobutyryl bromide in the presence of N,N'-diisopropylethylamine (DIPEA) and 4-N, N-(dimethylamino)pyridine (DMAP) in dichloromethane. These reaction mixtures were stirred at 0° C. for 1 hour, then at room temperature for 1 hour, to give 1 and 2 in 78 and 89% yields, respectively. In addition to these two ester-linked CPT initiators, glycine-linked initiators were prepared by reacting with BocGly-OH with CPT in the presence of N-(3-dimethylaminopropyl)-N'-ethylcarbodiimide hydrochloride (EDC). Boc-removal with trifluoroacetic acid (TFA) and reaction of the liberated amine with 2-bromoisobutyryl bromide generated initiator 3.

Polymerizations of MPC using these CPT-ATRP initiators were performed with a Cu(I)Br/bipyridine catalyst/ligand system in a DMSO-MeOH mixture at room temperature. Monomer conversion was monitored via $^1$H NMR spectroscopy, by integrating the vinyl protons of MPC against the methyl and methylene protons of the polymer backbone, using signals at 5.6 ppm ($CH_2=C$ on monomer), 6.1 ppm ($CH_2=C$ on monomer), 1.4-2.1 ppm ($CH_2$ on the polymer backbone) and 0.5-1.2 ppm ($CH_3$ on the polymer backbone). The CPT-polyMPC conjugates (copolymers) were isolated by precipitation into tetrahydrofuran (THF), and purified over a short silica column to remove residual copper. The DMSO-MeOH mixture was chosen to provide solution homogeneity throughout the course of the reaction (the initiators are soluble in DMSO, and the polymer in MeOH). Good initiator solubility is critically important for enabling clean polymerization kinetics that gave polymers of low PDI. Characteristic of a controlled polymerization, the polyMPC structures obtained displayed narrow PDI values (~1.2, as seen in FIG. 3) over a range of molecular weights from about 6 to about 17 kDa (Table 1), and number-average molecular weights ($M_n$) in agreement with monomer-to-initiator ratios (as judged by aqueous gel permeation chromatography (GPC) against PEO standards). Compared to 1 and 2, initiator 3 had low initiation efficiency, requiring long reaction times (about 48 hours) and giving higher-than-targeted molecular weights and higher PDI (1.34). This observation is consistent with literature reports on amide-containing ATRP initiators. (Li, et al. *Langmuir* 2005, 21 (22), 9946-9954; Adams, et al. *J. Polym. Sci. Pol. Chem.* 2008, 46 (18), 6082-6090.)

TABLE 1

CPT-terminated polyMPC prepared from CPT based initiators

| Polymer | Initiator | $N_{MPC}$ | Target $M_n$ | Conversion | $M_n$ | PDI | Diameter (nm) |
| --- | --- | --- | --- | --- | --- | --- | --- |
| HP1 | 1 | 20 | 6k | 93% | 6.5k | 1.21 | 5.0 |
| HP2 | 1 | 34 | 10k | 86% | 11k | 1.21 | 6.6 |
| HP3 | 1 | 70 | 21k | 91% | 17k | 1.40 | 7.9 |
| HP4 | 2 | 20 | 6k | 95% | 6.2k | 1.23 | 5.0 |
| HP5 | 2 | 34 | 10k | 62% | 9.3k | 1.23 | 5.5 |
| HP6 | 3 | 30 | 9k | 80% | 11k | 1.34 | 6.7 |

$N_{MPC}$: targeted number of MPC monomer units per polymer chain; Diameter: size as determined by DLS.

Figure 9:
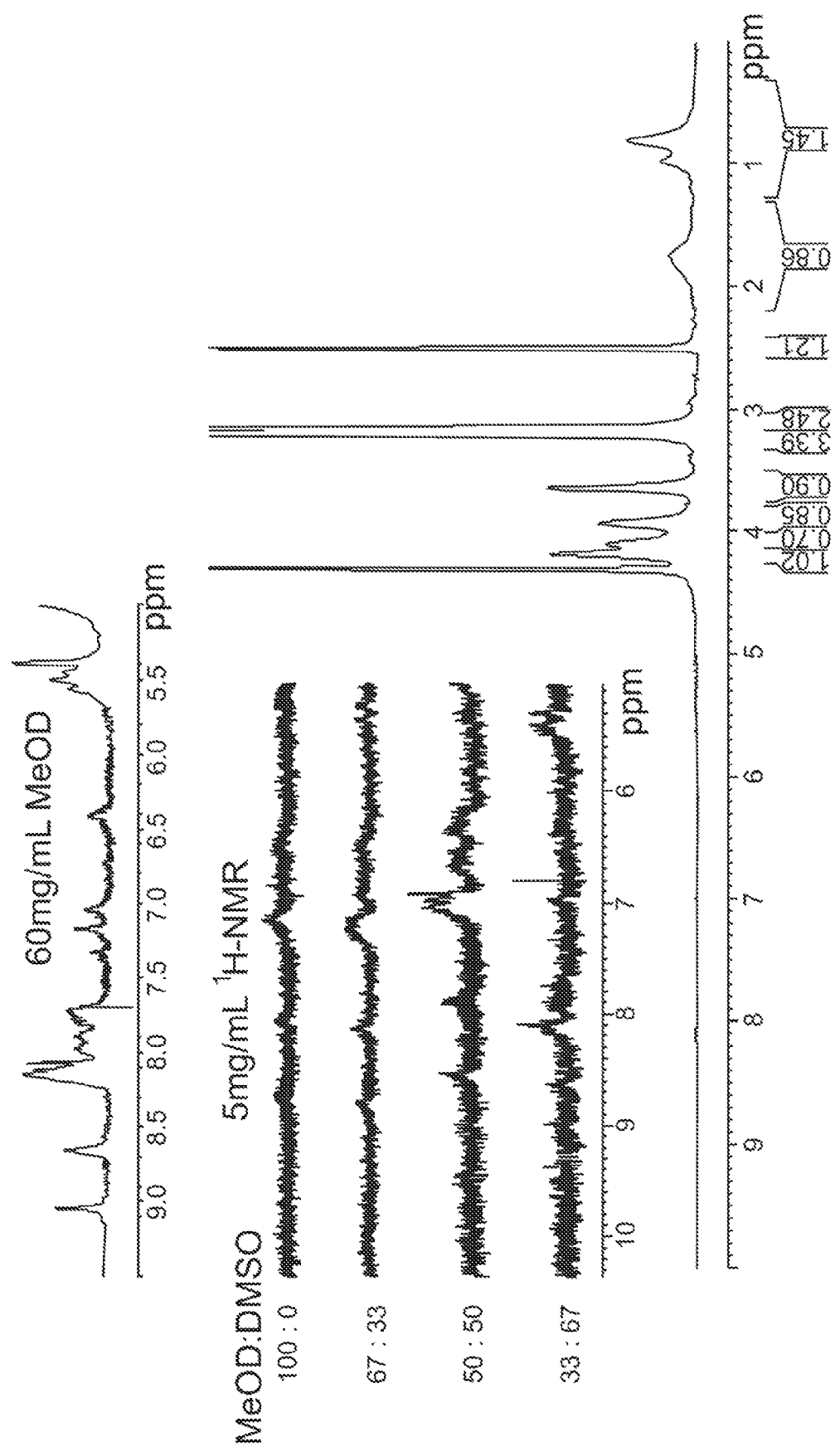
FIG. 9 shows exemplary data of $^1$H NMR spectra of CPT-polyMPC in $CD_3OD$.
Figure 10:
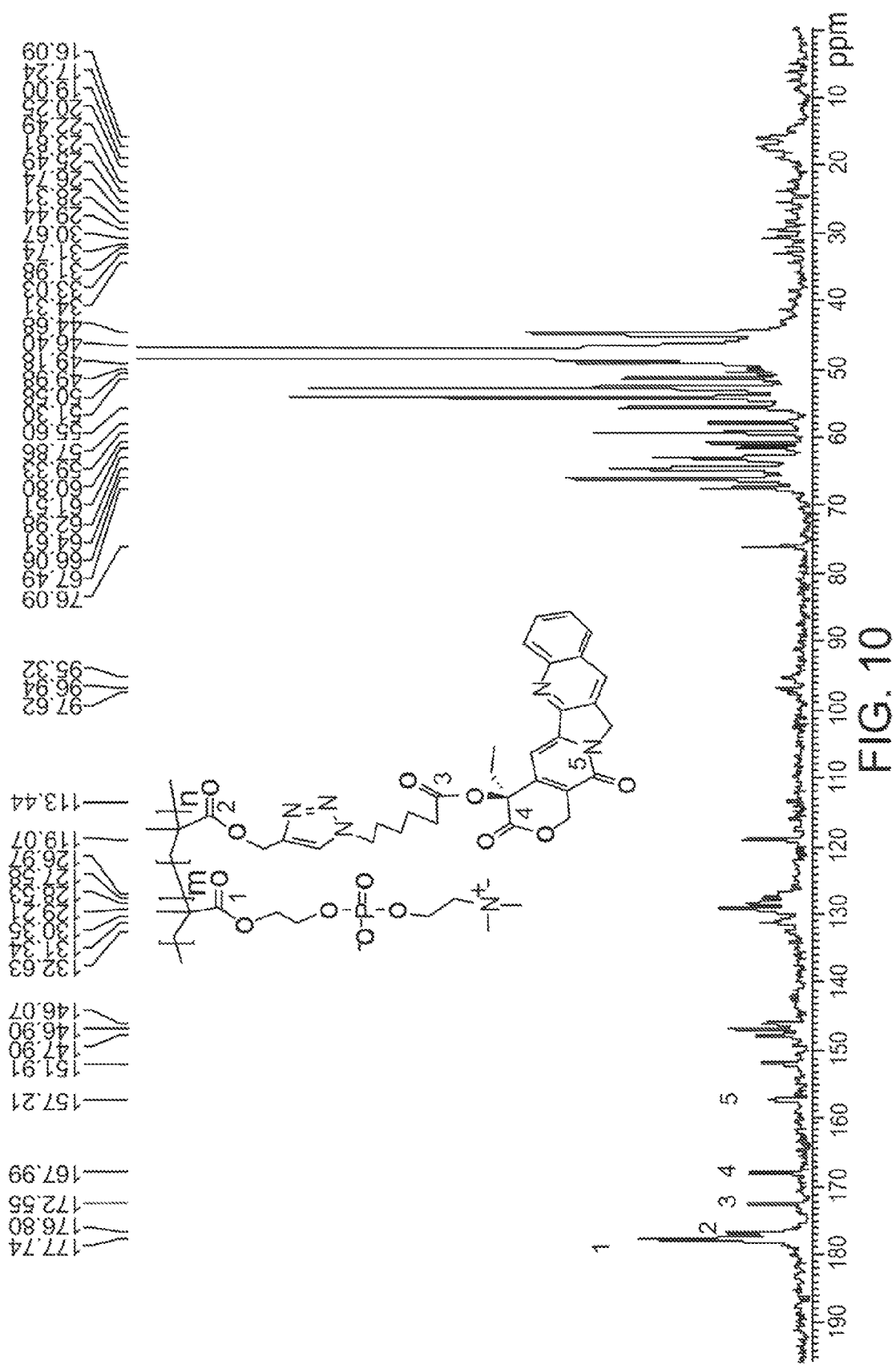
FIG. 10 shows exemplary data of $^{13}$C NMR spectrum of CPT-polyMPC(CP3) 100 mg/mL in $CD_3OD$.

CPT-terminated polyMPC is highly water soluble, as the hydrophilic zwitterionic structure easily overcomes the hydrophobicity of the CPT end-group. Preliminary dynamic light scattering (DLS) results suggest that dilute solutions (<20 mg/mL) of CPT-terminated polyMPC do not exhibit significant aggregation (i.e., are essentially molecularly dissolved), with estimated solution sizes in the range of about 5 to about 8 nm in diameter (Table $^1$H NMR analysis of CPT-polyMPC in $CD_3OD$ showed broad and weak aromatic CPT signals, in the range of about 7 to about 9 ppm (FIG. 9). Poor methanol solvation of the hydrophobic CPT component of the conjugate is likely responsible for this broadening, which precludes a reliable molecular weight estimation by NMR spectroscopic end-group analysis.

Syntheses of CPT-polyMPC conjugates. With confirmation that CPT can be used effectively in conjunction with ATRP conditions, and considering the prior work that demonstrated the amenability of CPT to click chemistry, CPT-polyMPC was prepared by combining these synthetic methodologies. (cf. Parrish, et al. *Bioconjugate Chem.* 2007, 18 (1), 263-267.) Copolymerization of MPC was chosen with trimethylsilyl (TMS)-protected propargyl methacrylate (TMS-PgMA), prepared from 3-TMS-propargyl alcohol and methacryloyl chloride. (Gao, et al. *Macromolecules* 2006, 39 (15), 4960-4965.) However, this method proved unsatisfactory, as the ethyl 2-bromoisobutyrate initiated ATRP copolymerization of MPC and TMS-PgMA gave copolymers with high PDI (nearly 2), and often multimodal elution peaks by GPC. Moreover, $^1$H NMR spectroscopy of these copolymers indicated a loss of the TMS protecting groups, likely the result of copper (I) acetylide formation during polymerization. Similar TMS deprotection and copper (I) acetylide formation has been observed in other polar organic solvents as well. (Ito, et al. *Tetrahedron Lett.* 1997, 38 (22), 3977-3980.) This undesired side-reaction promotes interchain coupling or even light cross-linking, and control experiments showed that the TMS protecting group was lost completely when TMS-PgMA was stirred in solution under typical ATRP conditions.

Considering the role of copper (I) acetylide as an intermediate in Cu(I)-catalyzed Huisgen azide-alkyne click cycloaddition, ATRP and click cycloaddition were carried out simultaneously, by introduction of CPT-azide at the outset of the polymerization. This one-pot ATRP/click reaction, shown in FIG. 4(a), used reaction conditions similar to those employed to prepare CPT-terminated polyMPC conjugates. Monomer conversion was monitored by $^1$H NMR spectroscopy, and cycloaddition was followed by disappearance of the CPT-azide N=N=N stretching signal at ~2100 cm$^{-1}$ in the FTIR spectrum. The CPT-polyMPC conjugates prepared in this fashion were purified by precipitation into THF, followed by passage over a short plug of silica gel in mixed solvents.

Figure 4C:
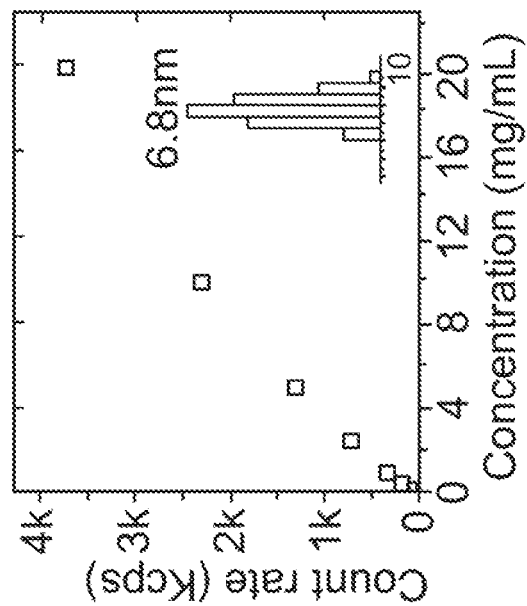
Figure 4B:
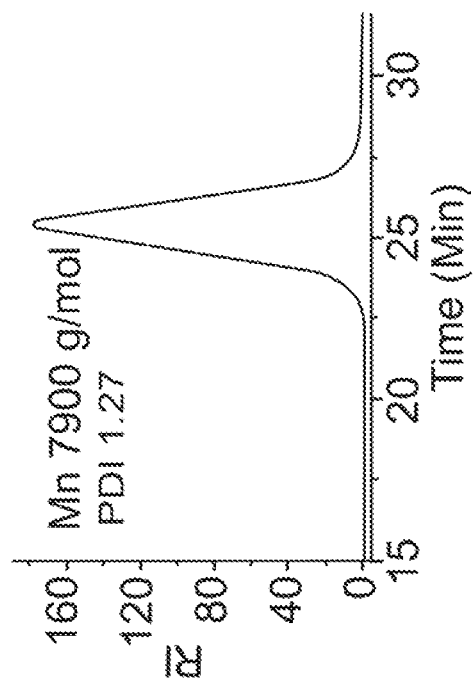
Figure 5B:
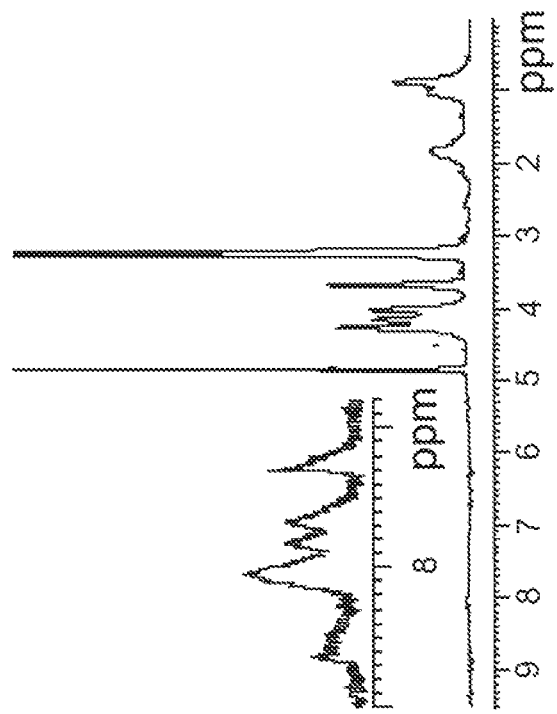
FIG. 5 shows exemplary (a) UV/Vis absorbance of the CPT-polyMPC conjugates at 1 mg/mL in DMSO-MeOH (1:1); (b) $^1$H NMR spectrum of CP1 in $CD_3OD$.
Figure 5A:
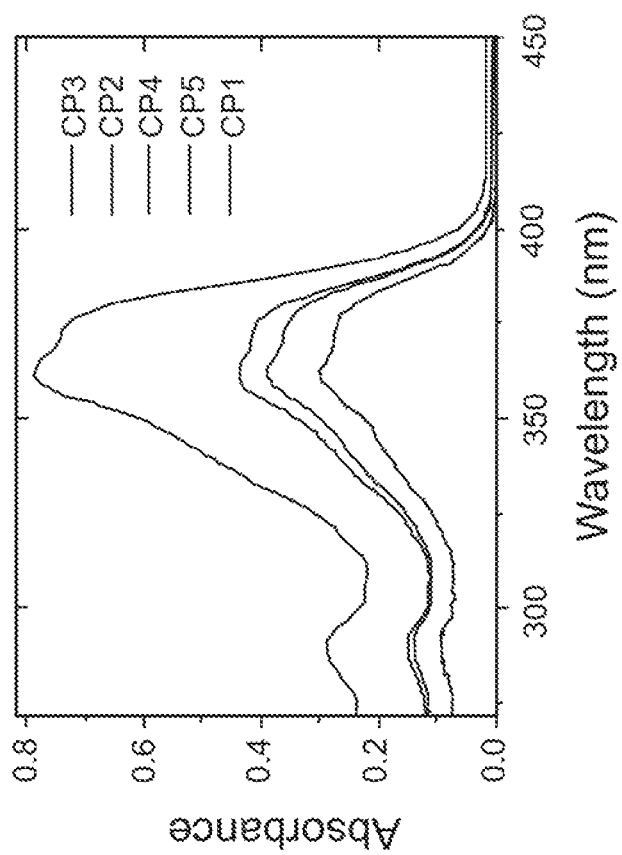
Figure 11:
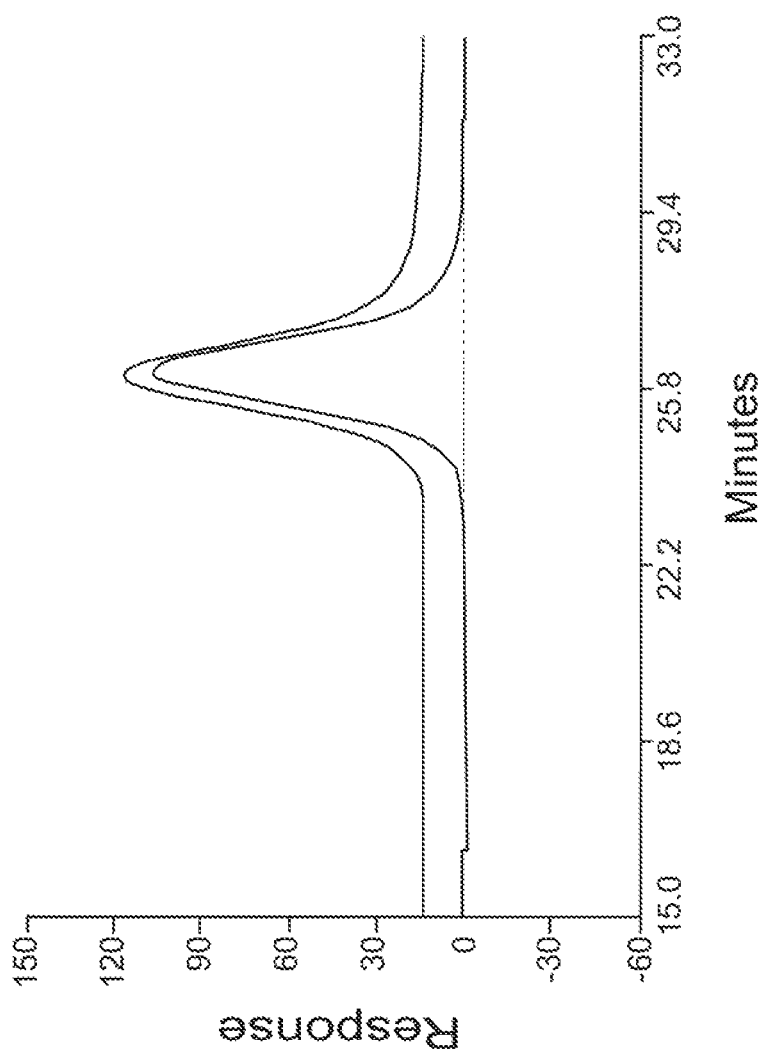
FIG. 11 shows exemplary data of aqueous GPC traces of CPT-polyMPC conjugates (CP3) with UV and RI channels.
Figure 12:
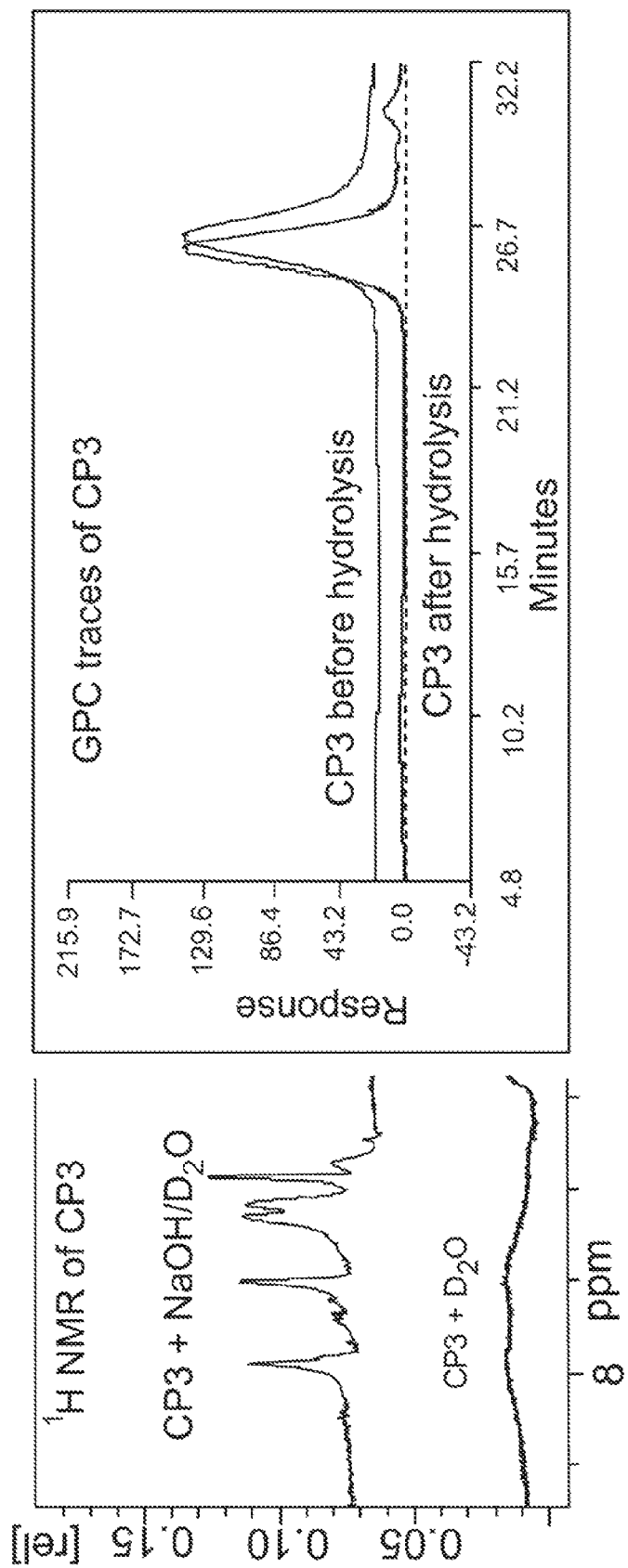
FIG. 12 shows exemplary data of $^1$H NMR spectra and GPC traces of CP3 in $D_2O$ before and after the CPTs were cleaved from polymer.

The CPT-polyMPC copolymers were characterized by aqueous GPC as shown in FIG. 4, and $^1$H and $^{13}$C NMR spectroscopy as shown in FIG. 5. The PDI values of the copolymers obtained by this one-pot procedure were in the range of about 1.25 to about 1.36, nearly comparable to the CPT-terminated polyMPC conjugates. A homogeneous distribution of CPT functionality throughout the polymer molecular weight distribution was confirmed by overlaying the UV and RI traces obtained from GPC characterization (FIG. 11). Aqueous solution sizes of these structures were also characterized using dynamic light scattering (DLS), with the copolymers largely forming unimers, in which the hydrophilic polymers are expected to cover a collapsed core of hydrophobic CPT groups. The CPT-polyMPC conjugates did not show a critical micelle concentration (CMC) up to 20 mg/mL, the highest concentration tested, and the average diameter of these structures was on average about 6.8 nm as shown in FIG. 4(c).

CPT loading on the polyMPC backbone may be varied by adjusting the MPC:TMS-PgMA/CPT ratio, as exemplified by the samples listed in Table 2, containing different levels of CPT loading. Importantly, PDI control was achieved at CPT loadings up to 14 weight percent (wt %) (compared to SN-38-PEG 4-arm stars containing 3.7 wt % CPT), and the aqueous solubility of this highly drug-loaded polyMPC structure was excellent (>250 mg/mL, or >35 mg/mL of CPT). The lactone form CPT alone has a solubility of 2.5 µg/mL. Thus, the polyMPC framework provides orders-of-magnitude greater solubility. (Zhao, et al. *Bioconjugate Chem.* 2008, 19 (4), 849-859.) Aqueous solutions of these conjugates exhibit viscosities that qualitatively resemble pure water, a notable difference from PEGylated drugs that often exhibit an undesirably high solution viscosity. The strongly hydrated zwitterionic moiety affects a wide variety of properties, from solubility to sliding friction, making these structures appealing for many biological applications including cancer drug delivery. (Chen, et al. *Science* 2009, 323 (5922), 1698-1701.)

The GPC-estimated molecular weight values of these CPT-polyMPC conjugates (calibrated against linear PEO standards) were lower than expected theoretically, suggesting a possible effect of intramolecular collapse of the hydrophobic pendent CPT groups in aqueous solution, perturbing solution size relative to homogeneous standards. When CPT groups were cleaved from the CPT-polyMPC conjugates, in a 1 N NaOH solution, the GPC-estimated molecular weights were actually seen to increase (Table 2). This observation can be rationalized by the homogeneous hydrophilic nature of the CPT-liberated polyMPC product relative to the CPT-grafted structure that consists of a hydrophilic backbone with pendent hydrophobic drug moieties.

$^1$H NMR spectroscopic analysis of these CPT-polyMPC conjugates in CD$_3$OD again presented difficulties in quantifying CPT incorporation, showing only weak aromatic CPT signals in the ~7-9 ppm range (FIG. 5). This chemical shift region also coincides with the expected proton resonance from the triazole generated by click cycloaddition. Light scattering studies on the MPC-CPT copolymers indicated the formation of polymer unimers, with diameters in the range of about 5 to about 10 nm (Table 2), in which the hydrophobic CPT moieties on a single chain collapse and are shielded by the hydrophilic MPC backbone. TEM experiments were also performed on the MPC-CPT copolymers, and small micelle-type structures were visualized. The shielding and desolvation of CPT causes the characteristic CPT protons to broaden significantly in the solution $^1$H NMR spectrum of these polymer-polyMPC conjugates. The intensity of the CPT peaks in the ~7-9 ppm region can be tuned by changing the NMR solvent. The CPT and MPC protons are best visualized in a 1:1 d6-DMSO/CD$_3$OD mixture (FIG. 9).

UV spectroscopy was found useful for estimating CPT loading. Recording the UV absorbance of the CPT-loaded polymer at 370 nm (FIG. 5(a)) allowed for the weight percent CPT in each polymer to be calculated, using known concentrations of the CPT-azide compounds and their molar extinction coefficients. The CPT loading for each sample is given in Table 2 as CPT weight percent. As expected, the relative absorbance at 370 nm from CPT increased with increasing amount of CPT incorporated, with experimental values corresponding closely to the theoretical CPT incorporation.

The CPT-polyMPC conjugate copolymers with different linkers between CPT and the polymer backbone, as depicted in Scheme 1, were synthesized to investigate drug release associated with ester linkages of variable neighboring hydrophilicity. For example, to contrast the case of the 6-azidohexanoic acid linker, 2-[2-(2-azidoethoxy)ethoxy]acetic acid was synthesized. This was done by oxidation of 2-[2-(2-chloroethoxy)ethoxy]ethanol to the corresponding carboxylic acid using Jones reagent at room temperature, followed by displacement of the chloride by reaction with NaN$_3$ at 80° C., to give azide 5 in 53% overall yield. The presence of the azide group was confirmed by its characteristic infrared spectral signal at ~2100 cm$^{-1}$, and the α-azido methylene ($\underline{CH}_2N_3$) resonance at 50.6 ppm in the $^{13}$C NMR spectrum. CPT azide compounds were obtained by acylation of CPT with linkers 4-6 in the presence of EDC and DMAP.

Fortunately, the linkers were found that have little-to-no effect on the polymerization and cycloaddition reactions, as indicated by the relatively low PDI values, and theoretical-to-experimental agreement in the drug loadings. Thus, this one-pot click/ATRP procedure provides an easy one-step process to introduce camptothecin into hydrophilic, biocompatible MPC polymers with good control over drug loading. While a one-pot simultaneous Cu(I)-catalyzed ATRP and "click" was reported for propargyl methacrylate and different

TABLE 2

CPT-polyMPC conjugates prepared by one-pot procedure

| Polymer | N$_{CPT}$ | CPT-Z-N$_3$ | Target CPT wt % | Conversion | M$_n$ | PDI | Diamter (nm) | UV Cal. CPT wt % | M$_n$' | PDI' |
|---------|-----------|-------------|-----------------|------------|-------|------|--------------|------------------|--------|------|
| CP1 | 1.4 | 6 | 5% | 94% | 5.2k | 1.27 | 5.3 | 5.1% | 6.8k | 1.17 |
| CP2 | 3 | 6 | 10% | 96% | 5.5k | 1.25 | 5.5 | 7.7% | 7.5k | 1.16 |
| CP3 | 5 | 6 | 15% | >98% | 5.1k | 1.36 | 5.7 | 13.8% | 7.5k | 1.17 |
| CP4 | 3 | 7 | 8.5% | >98% | 13k | 1.31 | 9.3 | 7.0% | 15k | 1.18 |
| CP5 | 3 | 8 | 8.4% | >98% | 7.0k | 1.26 | 6.8 | 5.1% | 9.0k | 1.16 |

N$_{CPT}$: number of CPT per polymer chain; CPT-Z-N$_3$: CPT azide compounds varying linker, Z: Conversion: average conversion of both monomers; M$_n$': number average molecular weight of polymer after CPT is cleaved from polymer by hydrolysis; PDI': PDI of polymer after CPT is cleaved from polymer by hydrolysis.

organic azide compounds, including 1-octyl azide, methoxytriethylene glycol azide, and 2"-azidoethyl-α-mannopyranoside, the TMS-protected alkyne has not, to our knowledge, been used in such click cycloadditions without prior deprotection. (Geng, et al. *Angew. Chem.-Int. Edit.* 2008, 47 (22), 4180-4183.) The facile deprotection, and rapid ensuing click reaction, allows the polymerization and click-conjugation to proceed cleanly and simultaneously, without complications associated with free radical polymerization in the presence of an alkyne.

Scheme 1

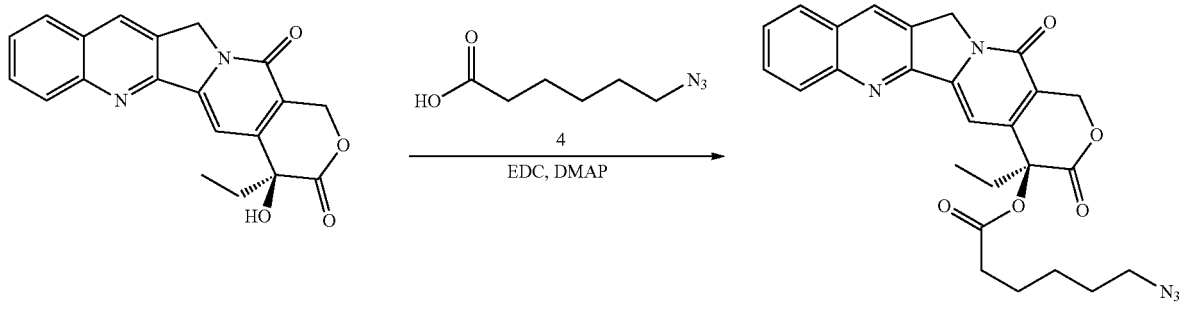

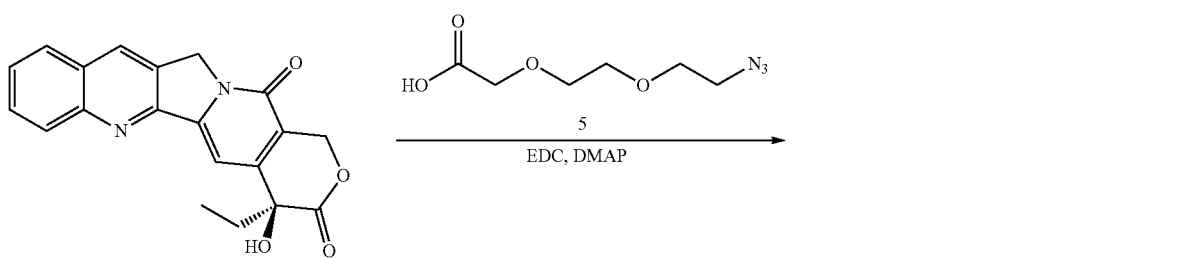

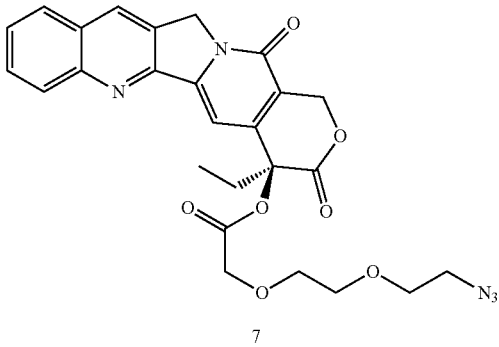

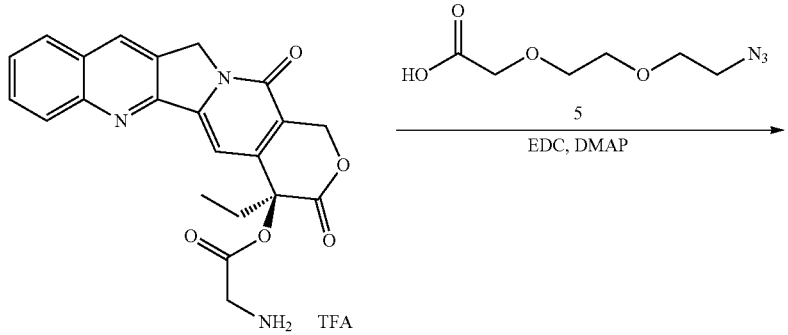

-continued

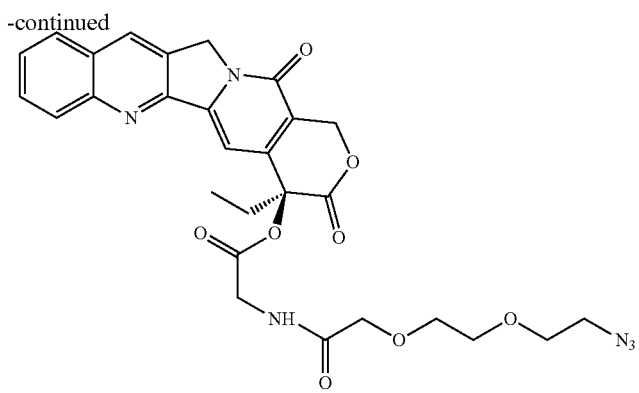

8

Syntheses of polyMPC-CPT conjugates have led to structures of higher molecular weight, as well as higher weight percentage of drug incorporation into the polymer backbone. A representative range of polymer-drug conjugates that have been synthesized is summarized in Table 3. The entries corresponds to P5/EiBB highlighted show an example of high molecular weight polymers, while the entries corresponds to P4/EiBB show an example of high drug loading. The upper range of molecular weight (as measured by GPC), for example, is ~50 kDa, and the upper range of drug loading about 18 weight percent.

TABLE 3

PolyMPC-CPT conjugates generated by one-pot polymerization/click method.

| Polymer | Initiator | M2 | $N_{MPC}$ | $N_{M2}$ | $N_{CPT}$ | CPT-Z | Target $M_n$ | Target CPT wt % | Conversion % | Conjugation % | GPC $M_n$ | PDI | UV CPT wt % |
|---|---|---|---|---|---|---|---|---|---|---|---|---|---|
| P1 | EiBB | 4 | 30 | 3 | 1.5 | 7 | 10k | 5.1 | 98 | <57 | 9k | 1.25 | 2.4 |
| P2 | EiBB | 5 | 60 | 5 | 5 | 10 | 20k | 8.2 | 99 | >87 | 11k | 1.54 | 8.4 |
| P3 | EiBB | 6 | 35 | 3 | 3 | 10 | 12k | 8.4 | 100 | N.D. | 8k | 1.27 | 6.9 |
| P4 | EiBB | 6 | 30 | 12 | 12 | 9 | 13k | 25 | 82 | >90 | 7k | 2.40 | 18 |
| P5 | EiBB | 6 | 100 | 5 | 5 | 9 | 30k | 5.3 | 92 | N.D. | 18k | 1.54 | 4.9 |
| P6 | EiBB | 6 | 200 | 5 | 5 | 9 | 60k | 2.8 | 92 | N.D. | 32k | 1.59 | 3.1 |
| P7 | EiBB | 6 | 300 | 5 | 5 | 10 | 90k | 1.9 | 90 | >90 | 50k | 1.58 | 1.4 |

M2: monomer 2. $N_{MPC}$: target degree of polymerization for MPC; $N_{M2}$: target degree of polymerization for monomer 2; $N_{CPT}$: target number of CPT compound per polymer; CPT-Z: camptothecin compound: Conversion %: average percentage of monomer conversion: Conjugation %: percentage of camptothecin grafted into the polymer. UV CPT wt %: camptothecin weight percentage loading determined by UV spectroscopy.

Polymers Generated from One-Pot Method Using the NHS ATRP Initiator

In addition to using ethylisobutyrylbromide (EiBB) as the ATRP initiating moiety, an N-hydroxysuccinimide (NHS) initiator is also found to be useful for post-polymerization modifications, such as conjugation to a protein or antibody for targeting purposes (Scheme 2).

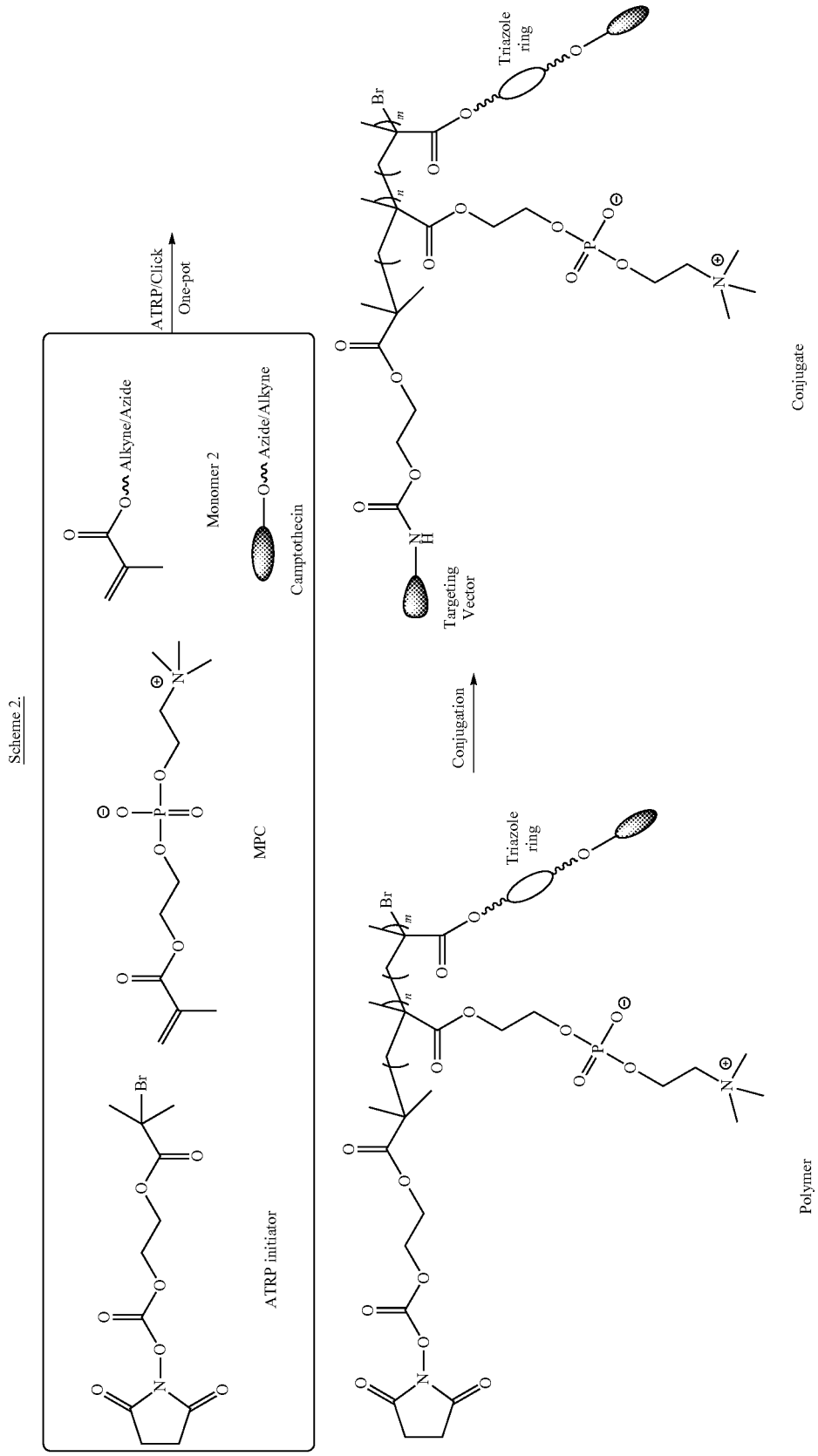

Polymer-drug conjugates with NHS chain-ends were synthesized, and the data is summarized in Table 4. These polymers show good molecular weight control, polydispersity, and drug loading.

TABLE 4

Polymers generated from one-pot method using the NHS ATRP initiator

| Polymer | Initiator | $M_2$ | $N_{MPC}$ | $N_{M2}$ | $N_{CPT}$ | CPT-Z | Target $M_n$ | Target CPT wt % | Conversion % | Conjugation % | GPC $M_n$ | PDI | UV CPT wt % |
|---|---|---|---|---|---|---|---|---|---|---|---|---|---|
| P3 | NHS | 6 | 30 | 3 | 3 | 8 | 10k | 9.7 | 100 | N.D. | 5k | 1.26 | 8.0 |
| P9 | NHS | 6 | 30 | 5 | 5 | 8 | 11k | 14 | 100 | N.D. | 5k | 1.36 | 14 |
| P10 | NHS | 6 | 60 | 5 | 5 | 9 | 20k | 8.3 | 91% | N.D. | 9k | 1.30 | 8.8 |
| P11 | NHS | 6 | 20 | 5 | 5 | 9 | 8k | 19 | 100% | N.D. | 5k | 1.40 | 17 |

M2: monomer 2. $N_{MPC}$: target degree of polymerization for MPC; $N_{M2}$: target degree of polymerization for monomer 2; $N_{CPT}$: target number of CPT compound per polymer; CPT-Z: camptothecin compound; Conversion %: average percentage of monomer conversion; Conjugation %: percentage of camptothecin grafted into the polymer. UV CPT wt %: camptothecin weight percentage loading determined by UV spectroscopy.

Conjugation to polyMPC-CPT structures through the NHS end-group was performed with the protein lysozyme as an example case, and the polymer-protein conjugates were purified using fast protein liquid chromatography equipped with a cation exchange column. The loading of conjugate was calculated using UV absorbance at 280 and 370 nm. The results were summarized in the Table 5.

TABLE 5

Conjugation reaction, drug per conjugate (DPC) and polymer per conjugate analysis

| Conjugate | Polymer | Protein | Ratio | Reaction time | DPC | PPC |
|---|---|---|---|---|---|---|
| C1 | P8 | Lysozyme | 10 | Overnight | 5.6 | 1-2 |
| C2 | P8 | Lysozyme | 20 | Overnight | 14.4 | 4-5 |
| C3 | P10 | Lysozyme | 20 | Overnight | 4.8 | 1 |
| C4 | P11 | Lysozyme | 20 | Overnight | 7.2 | 1-2 |
| C5 | P10 | Lysozyme | 20 | 2 h | 3.7 | 0.7 |

C1-C5 here refer to the conjugates

Synthesis of PolyMPC-Doxorubicin conjugates Doxorubicin (DOX)-polyMPC conjugates were synthesized by a one-pot ATRP/click procedure. These polymer-drug conjugates are designed to alter the pharmacokinetics of doxorubicin, and increase its therapeutic index by decreasing the side effects associated with administration of the free (unconjugated) drug). The DOX was modified with 6-azidohexane-hydrazide as the linker, as shown in Scheme 3. The hydrazine group reacts with DOX through the carbonyl group, forming a hydrazone bond, which is pH sensitive. This new linkage between the DOX and polymer is different from the ester bond in the polyMPC-CPT conjugate offering some advantages. The DOX is expected to release from the polymer backbone at low pH, after the polymer accumulates in the tumor environment, while the conjugate will predominantly stay intact at physiological pH during circulation.

Scheme 3

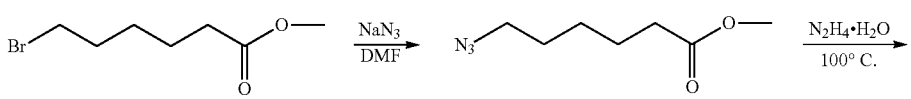

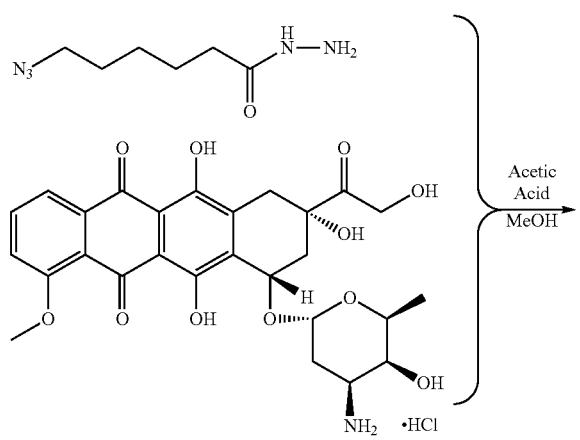

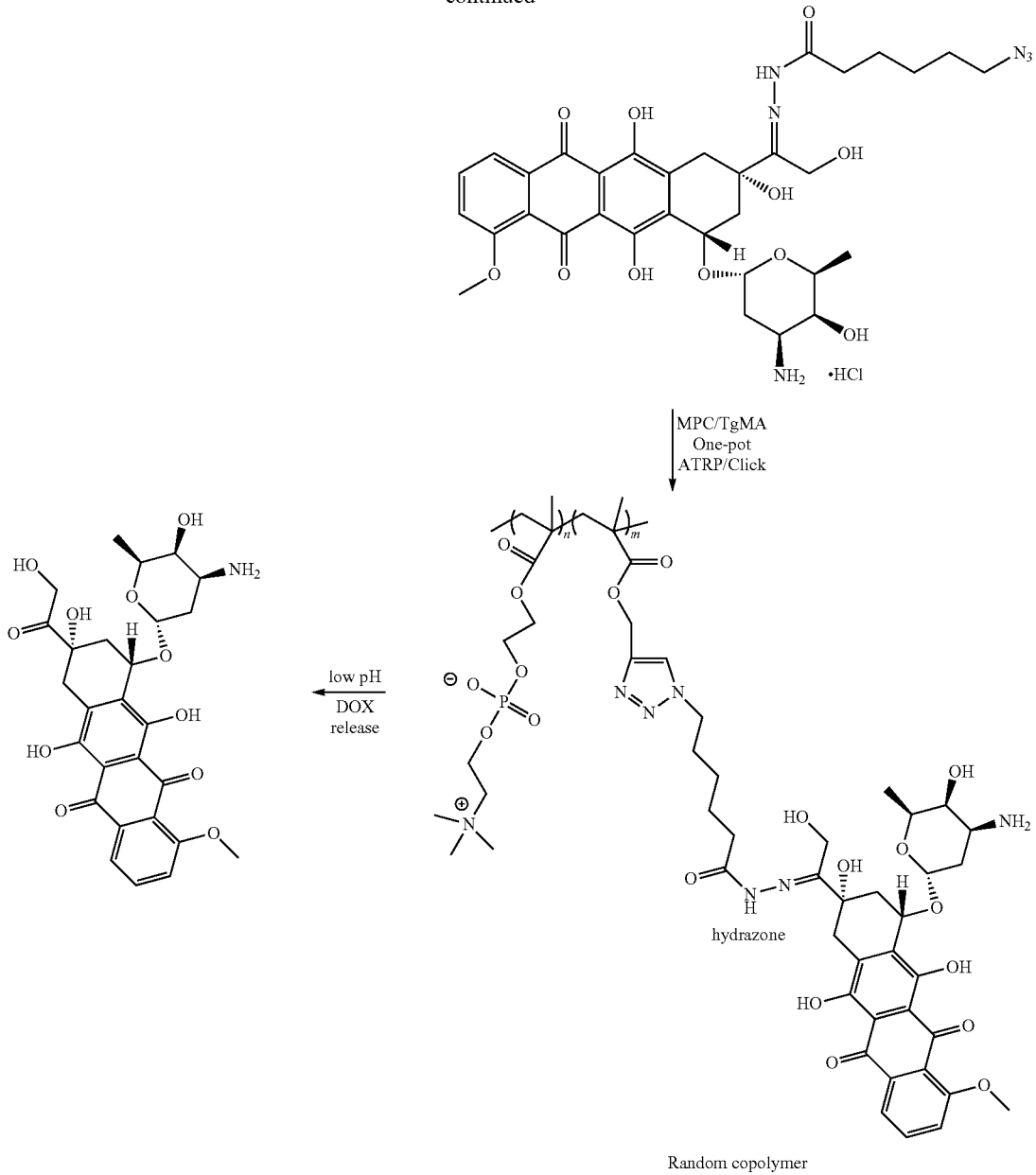

Random copolymer

Methyl 6-bromohexanoate was reacted with sodium azide to give methyl 6-azidohexanoate, then converted to the corresponding hydrazide using hydrazine hydrate. The linker compound 6-azidohexanehydrazide was conjugated with DOX hydrochloride in dry methanol, with a drop of acetic acid, forming the desired DOX-azide compound. The one-pot method polymerization/click method shown in the scheme was used to synthesize the new DOX-polyMPC copolymer. The polymer was characterized with NMR spectroscopy and GPC, while drug weight percent was measured using a UV method.

Drug release from polyMPC-CPT conjugates. In vitro drug release studies were performed on polyMPC-CPT conjugates to gauge their relative release rates and potential utility in delivery applications. To begin, CPT-terminated polyMPC materials were incubated in PBS at various buffered pH values (5.5, 7.4, and 9.1) to measure the CPT hydrolysis half-lives from the polymer backbone. Polymers prepared from the CPT initiator 1 (one methyl group) showed slow CPT release, while the release rate increased with increasing pH. No CPT was released at pH 5.5, and only 4.5% was released at pH 7.4 at time=30 days. In human plasma, containing various enzymes that can aid in drug cleavage, 50% of the drug was released in 10 days. Interestingly, no CPT release was detected from the polymer prepared from the CPT initiator 2 (two methyl groups), pointing to the importance of the local steric environment around the key ester bond. Integrating a glycine linkage between the polymer and CPT did little to accelerate ester bond cleavage and drug release.

Figure 7:
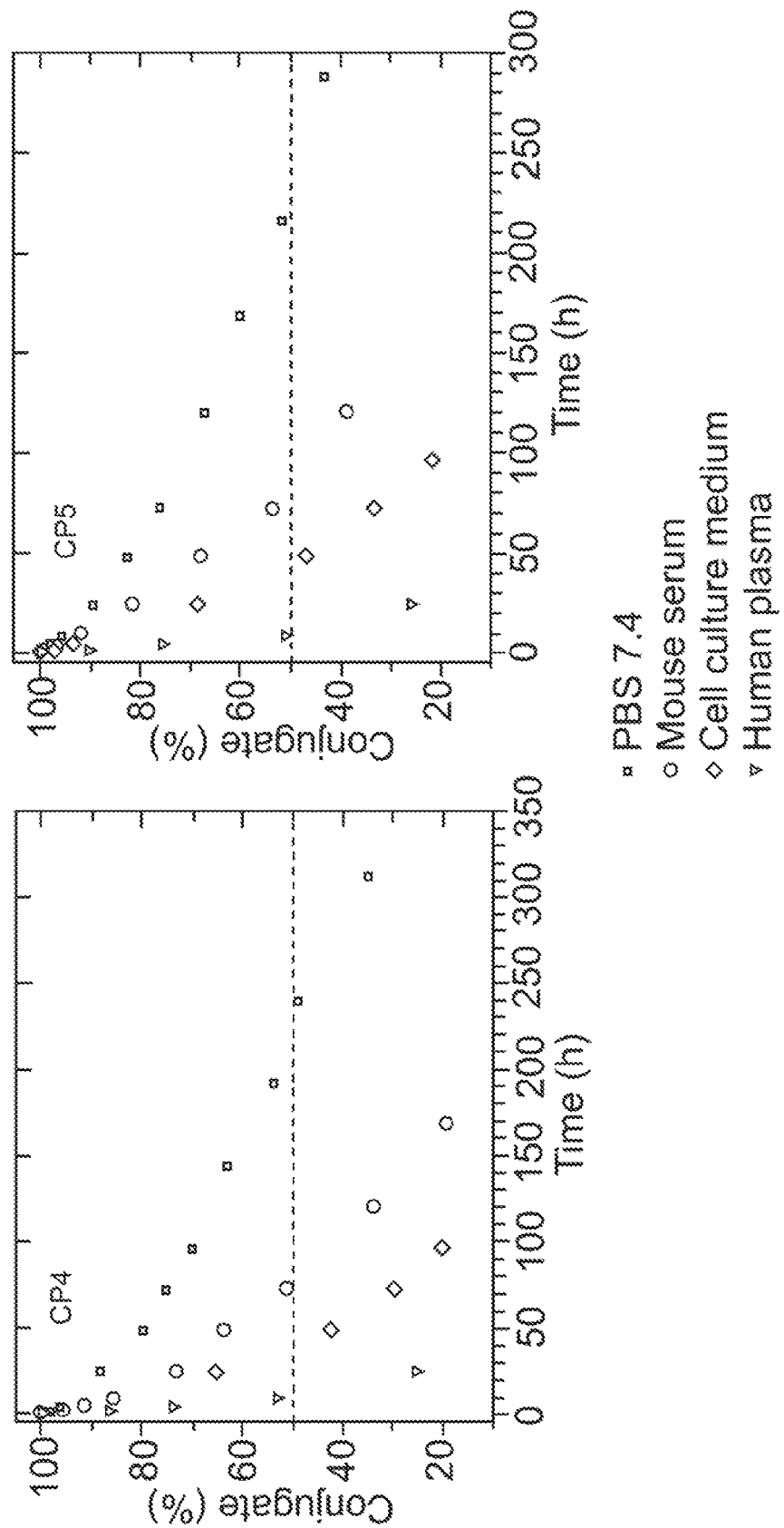
FIG. 7 shows an exemplary conjugate (CP4 and CP5) degradation over time in different media at 37° C.

For the polyMPC-CPT conjugates, the choice of backbone-to-drug linkage led to significant changes in ester cleavage and drug release. The hydrophobic 6-azidohexanoic acid linker was first chosen for CPT conjugation, giving copolymers CP1, CP2 and CP3. These structures gave very little hydrolysis over 4 days incubation under several different aqueous conditions, suggesting that this linker is probably too hydrophilic for potential future in vivo use. To expedite ester hydrolysis, the hydrophilic linker 2-[2-(2-azidoethoxy)ethoxy]acetic acid was used to prepare copolymers CP4 and CP5. These results of hydrolysis studies of these structures in different media are shown in FIG. 7 and Table 6. For example, SEC-HPLC traces of CP4 incubated in cell culture medium is shown in FIG. 6(a), where the polymer-drug conjugate elutes at 9.4 min. and the free CPT elutes at 16.9 min. Over the course of 96 hr., the conjugate peak is seen to decrease while the CPT peak increases as expected when CPT is hydrolyzed from the polymer backbone. The reverse phase HPLC analysis of the copolymers after incubation is shown in FIG. 6(b), confirming the release of CPT. These copolymers, with half-lives of 210-220 h. in PBS (pH 7.4), showed much faster release profiles than the CPT-polyMPC homopolymers and CPT-polyMPC copolymers prepared from 6-azidohexanoic acid linker. These polymers showed significantly shorter half-lives in mouse serum (~80 h), cell culture medium (~40 h) and human plasma (~8-9 h). The hydrophilicity and electron-withdrawing effect of the alkoxy group a to the carboxylic acid aids in accelerating ester cleavage.

TABLE 6

Half lives of CPT-polyMPC conjugates with hydrophilic linkers in different media

|  | Medium | PBS 7.4 | Mouse serum | Cell Culture Medium | Human Plasma |
|---|---|---|---|---|---|
| $T_{1/2}$ | CP4 | 212 h | 80 h | 43 h | 8.4 h |
|  | CP5 | 220 h | 76 h | 37 h | 9.0 h |

Cell Culture Assays Using PolyMPC-CPT Conjugates

Figure 8B:
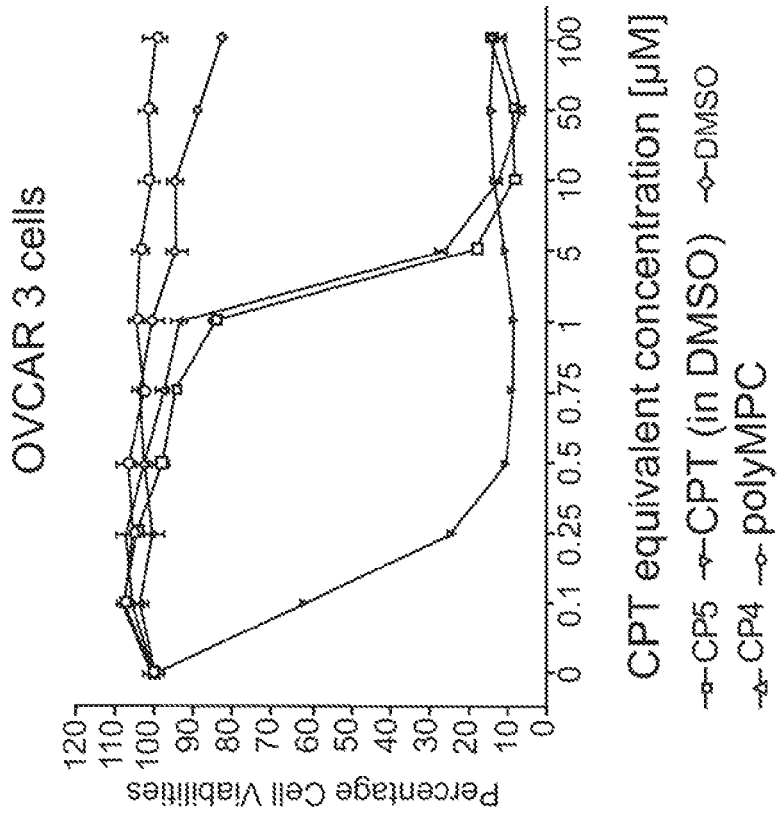
FIG. 8 shows exemplary in vitro cytotoxicity of CPT-polyMPC conjugates in cell culture of human breast (MCF-7), ovarian (OVCAR 3) and colon (COLO 205) adenocarcinoma cells, shown in FIG. 8(A), FIG. 8(B) and FIG. 8(C), respectively.
Figure 8A:
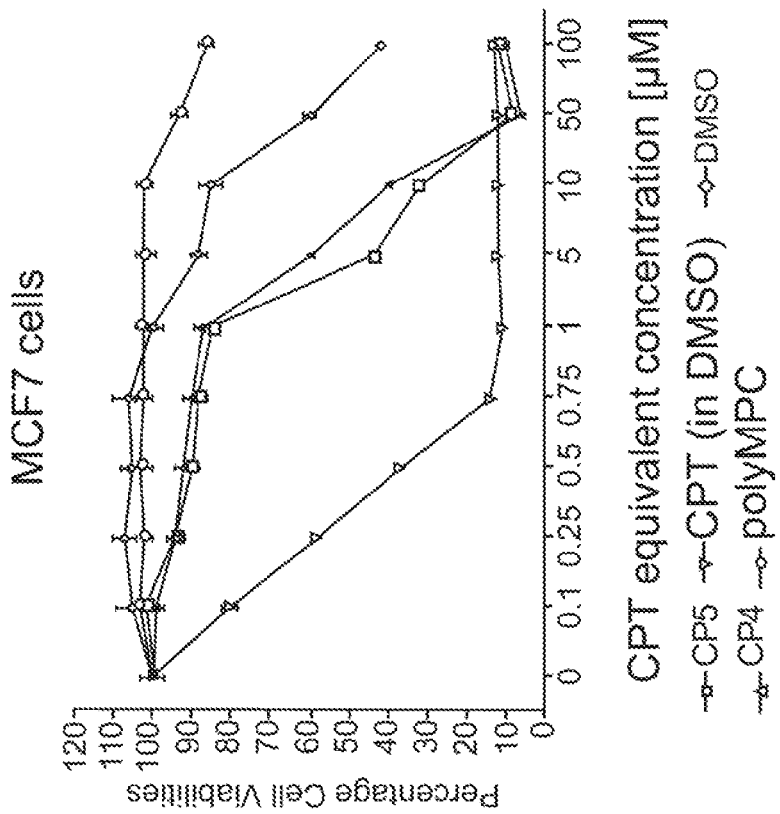
Figure 8C:
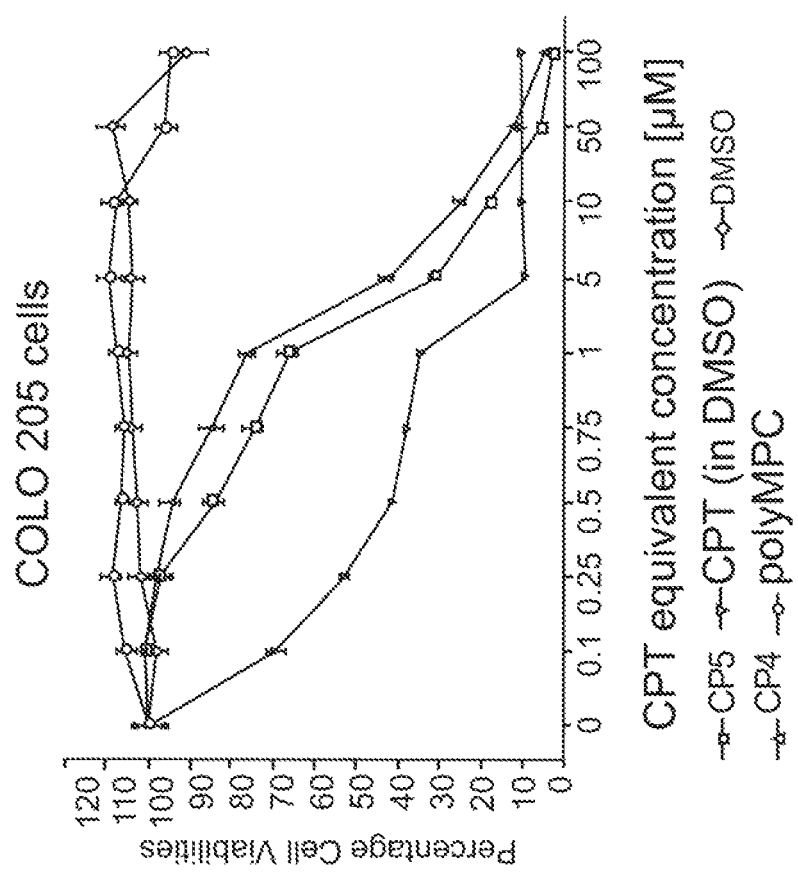

HPLC characterization of CPT liberation from CPT-polyMPC conjugates confirmed the importance of tailored linkers, and was informative for in vitro cell culture evaluation of conjugate toxicity against various cell lines. Taking CP4 and CP5 as examples, both containing 7 linkers, one ester-linked (9) and the other glycine-linked (10), a much faster CPT release profile was seen in human plasma as compared to CPT release rates in PBS. These CPT hydrolysis half-lives are, however, slower than those reported for PEGylated-SN38 conjugates, leading to an expected longer blood circulation time in vivo. (Zhao, et al. *Bioconjugate Chem.* 2008, 19 (4), 849-859.) The anti-cancer activity of these polyMPC conjugates (CP4 and CP5) was tested against different cancer cell lines, including human breast (MCF-7), ovarian (OVCAR 3) and colon (COLO 205) adenocarcinoma cells. This was done by incubating CPT-equivalent concentrations of CP4 and CP5 with these cells for 72 h., followed by cell viability measurements using a luminescence plate reader (see Experimental Section). Controls included a DMSO solution of CPT, and polyMPC itself in sterile distilled water. Dose response curves showed that both CP4 and CP5 were potent against the cancer cell lines tested here. Importantly, the cytotoxicity was through the CPT only, since polyMPC by itself was non-toxic (FIG. 8). The $IC_{50}$ values in Table 7 show that both CP4 and CP5 induced cytotoxicity at $IC_{50}$ values higher than native CPT alone, resulting from the fact that CPT was slowly liberated over time from the polymer chain. From Table 7 it can also be seen that the colon cancer cells were most sensitive to the CPT-polyMPC copolymers ($IC_{50}$ CP4 3.9 and CP5 2.3 µM).

TABLE 7

$IC_{50}$ values (µM) of CPT-polyMPC conjugates across various cancer cell lines.

| Cell type | CP4 | CP5 | CPT |
|---|---|---|---|
| MCF-7 | 6.7 | 4.6 | 0.29 |
| OVCAR-3 | 3.3 | 2.5 | 0.13 |
| COLO 205 | 3.9 | 2.3 | 0.32 |

Synthesis of Azide Containing PolyMPC

Figure 13A:
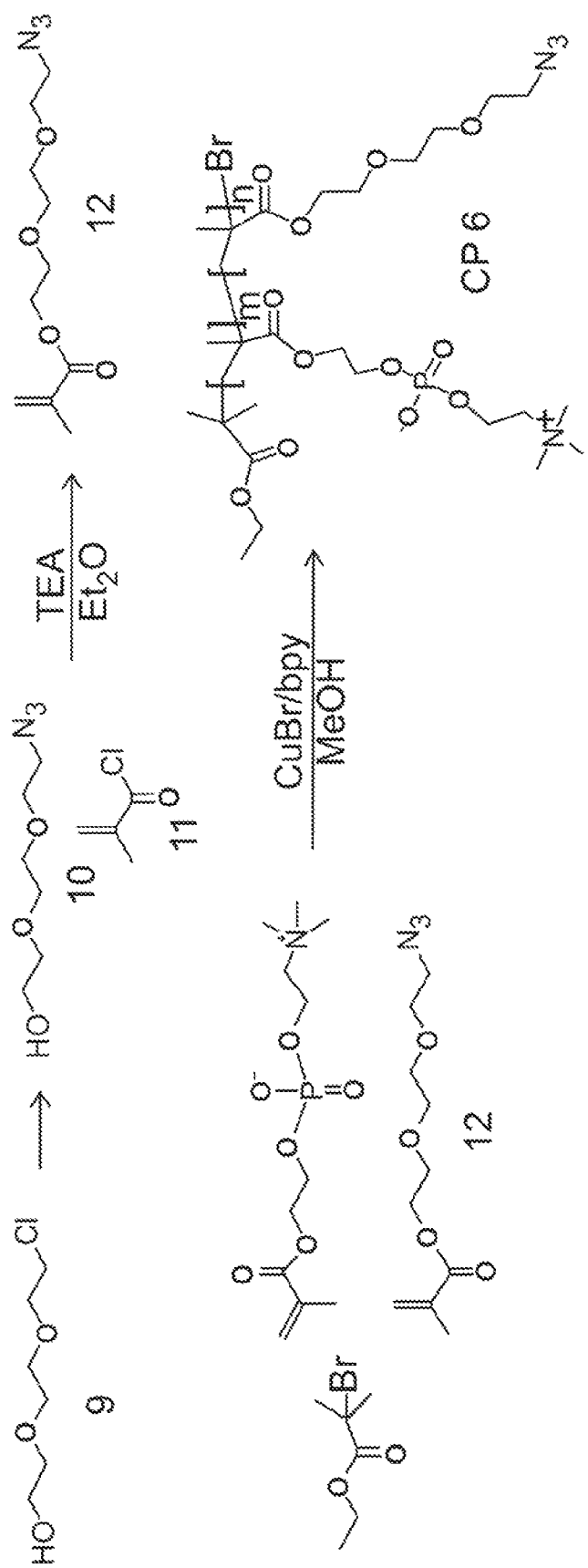
FIG. 13 shows exemplary synthesis route of hydrophilic azide containing polyMPC polymer CP6 (a); IR characterization of CP6 showing the incorporation of azide group into the polymer (b); aqueous GPC trace of CP6 (c).
Figures 13B, 13C:
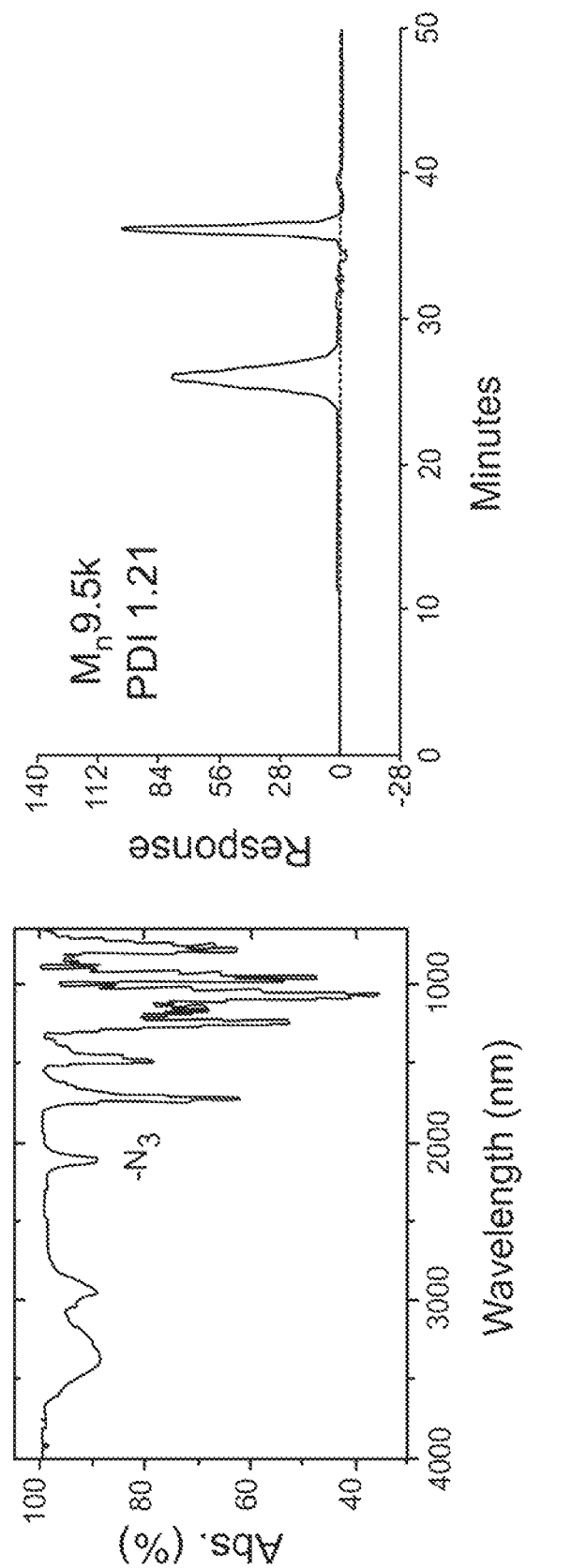

In another aspect of the invention, an alternate way to introduce CPT onto the polyMPC is provided (FIG. 13). Azide-containing monomer 12 was firstly synthesized by reaction between methacryloyl chloride 11 and 2-[2-(2-azidoethoxy)ethoxy]ethanol 10, which was synthesized by reaction of 2-[2-(2-chloroethoxy)ethoxy]ethanol 9 with sodium azide, as shown in FIG. 13(a). MPC and monomer 12 were copolymerized with EBiB as ATRP initiator in methanol using a similar ATRP procedure as described before. The copolymer CP6 was obtained by purification on silica-gel column followed by characterization with $^1$H NMR, FT-IR and aqueous GPC. The absence of alkyne group precluded the possibility of side-chain coupling as indicated by the low PDI value (1.21) shown in FIG. 13. The incorporation of azide group was verified by the IR signal at 2100 cm$^{-1}$, while integration of the $^1$H NMR spectrum showed about 22 mol % azide incorporation, closely matching the monomer feed ratios (25 mol % azide). Polymer molecular weights estimated by aqueous GPC matched the monomer-to-initiator ratio. This new azide containing polyMPC copolymer offers a higher molar percentage of functionality for click chemistry, which may be used to conjugate various alkyne-containing compounds, including alkyne-substituted drugs, using click chemistry.

CPT Alkyne Conjugation to PolyMPC Through Click Chemistry

Figure 14D:
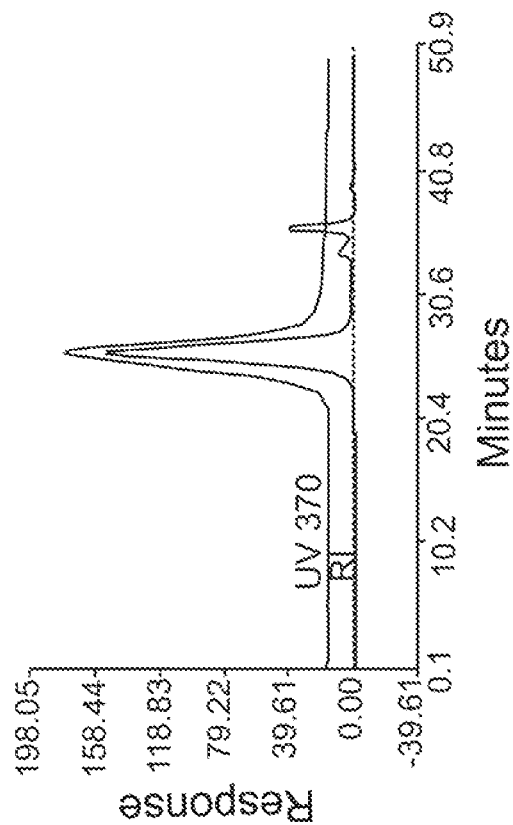
FIG. 14(d) shows GPC traces of the CP7 recorded in RI channel (dark) and UV 370 nm channel (light).
Figure 14C:
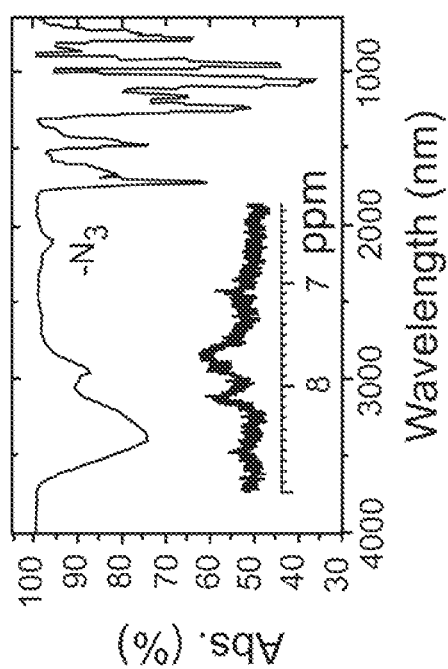
FIG. 14(c) shows IR characterization of the CPT-polyMPC CP7 (insert is the NMR spectrum showing the protons from CPT moiety)

Camptothecin was modified to alkyne derivative 14 by coupling the CPT-Gly with 4-pentynoic acid using EDC/DMAP in DCM with a yield of 74% and the hydrophobic CPT alkyne compound 14 was conjugated with azide containing polyMPC copolymer CP6 in DMSO/MeOH mixture solvent with CuBr/bpy as catalyst system, as depicted in FIG. 14. The cloudy reaction mixture slowly turned clear, indicating conjugation of CPT-alkyne 14 to the soluble CP6. Unconjugated 14 was removed by precipitation into THF, and the conjugate CP7 was further purified by column chromatography to remove the catalysts. IR characterization of the purified conjugate showed the presence of some residual azide, as shown in FIG. 14(c). These unreacted azide groups provide the opportunity to further incorporate targeting groups or other cancer drugs. The $^1$H NMR spectrum of CP7 also showed a broad signal from CPT at low field (around 8 ppm), as seen for the conjugates prepared in the one-pot method. An overlay of the aqueous GPC traces from the RI and UV 370 nm detectors matched closely, further verifying the successful conjugation as shown in FIG. 14(d). The CPT loading calibrated from UV spectroscopy (13.8 wt %) is in excellent agreement with the targeted value (14 wt %).

This two-step method provides an alternative, complimentary approach to the alkyne-substituted polyMPC method. Partial reaction of the azide groups in the polymer leaves residual azide that may be conjugated to other drugs, targeting groups, etc.

Experimental

Materials.

Sodium azide, 4-(dimethylamino)pyridine (DMAP), N,N'-diisopropylethylamine (DIPEA), triethylamine (TEA), N-(3-Dimethylaminopropyl)-N'-ethylcarbodiimide hydrochloride (EDC), 2-bromopropionyl bromide, 2-bromoisobutyryl bromide, copper(I) bromide, 2,2'-bipyridine (bpy), 6-bromohexanoic acid, 2-[2-(2-chloroethoxy)ethoxy]ethanol, ethyl 2-bromoisobutyrate, 3-(trimethylsilyl)propargyl alcohol, methacyloyl chloride, mouse serum, and human plasma were purchased from Aldrich. 20(S)-camptothecin (CPT) was purchased from Acros. Chromium trioxide was purchased from Alfa Aesar. TFA was purchased from Fisher Scientific. Boc-Gly-OH was purchased from Advanced ChemTech. MPC monomer was synthesized in house. Dichloromethane (DCM) was distilled over $CaH_2$. All other materials were used without additional purification. The human colon (COLO 205), ovarian (OVCAR 3) and breast (MCF-7) adenocarcinoma cells were purchased from American Type Culture Collection (ATCC), whereas RPMI 1640 and MEM cell culture media was purchased from Invitrogen and Mediatech respectively. Fetal bovine serum (FBS) was purchased from Atlanta biologicals and bovine insulin from Aldrich. Cell viability was measured using CellTiter-Glo luminescent cell viability assays (Promega).

Instrumentation.

NMR spectra were recorded on Bruker DPX300 spectrometer ($\omega_{13C}$=0.25 $\omega_{1H}$). High-resolution mass spectral (HRMS) data were obtained on a JEOL JMS700 MStation. UV/Vis absorbance measurements were taken on a Perkin-Elmer Lambda 25 UV/Vis spectrometer. IR absorbance data were obtained on a Perkin-Elmer Spectrum One FT-IR spectrometer equipped with a universal ATR sampling accessory. Dynamic light scattering was performed on Malvern Zetasizer Nano-ZS and transmission electron microscopy (TEM) was performed on JEOL 2000 FX MARK II 200 keV transmission electron microscope. Molecular weights and polydispersity indices (PDIs) were estimated by gel permeation chromatography (GPC) in sodium nitrate (0.1 M with 0.02 W % of $NaN_3$) aqueous solution against poly(ethylene oxide) standards, operating at 1.0 mL/min with an HP Series 1050 Pump, HP 1047A refractive index detector, and three Waters Ultrahydrogel Linear columns (300×7.8 mm). The HPLC system was consisted of Waters Alliance system with 2996 photodiode array detector. A size exclusion column Shodex KW-803 eluting with 10% ethanol in PBS buffer (pH 7.4) at a flow rate of 1 mL/min and a reverse phase C18 column (250×4.6 mm) eluting with a gradient of 5-95% of acetinitrile in 0.05% TFA at a flow rate of 1 mL/min were used to analyze samples.

Synthesis of CPT-PolyMPC Homopolymer

Synthesis of Initiator 1.

CPT (600 mg, 1.72 mmol) and DIPEA (445 mg, 3.45 mmol) were suspended in 30 mL of dry DCM. After adding DMAP (440 mg, 3.45 mmol), the suspension was cooled to 0° C. 2-bromopropionyl bromide (745 mg, 3.45 mmol) in 20 mL of dry DCM was added to the suspension dropwise. The reaction mixture was stirred at 0° C. for 1 h then room temperature for 1 h. After washing with 1 N HCl (50 mL×3), 1% $NaHCO_3$ (50 mL×3), and brine (50 mL×1), the organic phase was dried over $MgSO_4$ and then filtrated. Evaporation of the solvent by rotary evaporation gave crude product, which is recrystallized from $MeOH/CH_2Cl_2$ (95:5) to give compound 1 (650 mg, 78% yield) as light yellow solid. $^1H$ NMR ($CDCl_3$, 300 MHz): δ 8.44 (s 1H), 8.29 (d, J=8.7 Hz, 1H), 7.97 (d, J=8.1 Hz, 1H), 7.86 (t, J=7.5 Hz, 1H), 7.70 (t, J=7.2 Hz, 1H), 7.52 (s 1H), 5.73 (d, J=17.4 Hz, 1H), 5.43 (d, J=17.4 Hz, 1H), 5.32 (s 2H), 4.62 (q, J=6.9 Hz, 1H), 2.16-2.41 (m, 2H), 1.86 (d, J=6.9 Hz, 3H), 1.03 (t, J=7.5 Hz, 3H). $^{13}C$ NMR ($CDCl_3$, 75 MHz): δ 169.0, 167.1, 157.3, 152.2, 148.8, 146.4, 145.0, 131.2, 130.7, 129.8, 128.4, 128.1 (2C), 120.2, 96.2, 76.9, 67.2, 50.0, 38.7, 31.8, 21.1, 7.6. HRMS-FAB (m/z): $[M+H]^+$ calculated for $C_{23}H_{20}BrN_2O_5$: 483.0556, found: 483.0587.

Synthesis of Initiator 2. CPT (300 mg, 0.86 mmol) and DIPEA (222 mg, 1.72 mmol) were added into 20 mL of dry DCM. After adding DMAP (210 mg, 1.72 mmol), the suspension was cooled to 0° C. 2-bromoisobutyryl bromide (594 mg, 2.58 mmol) in 10 mL of dry DCM was added to the suspension dropwise. The reaction mixture was stirred at 0° C. for 1 h then room temperature for 1 h. After washing with 1 N HCl (40 mL×3), 1% $NaHCO_3$ (40 mL×3), and brine (40 mL×1), the organic phase was dried over $MgSO_4$. The solvent was removed under reduced pressure to give crude product, which is recrystallized from $MeOH/CH_2Cl_2$ (95:5) to give pure compound 2 (300 mg, 89% yield) as light yellow solid. $^1H$ NMR ($CDCl_3$, 300 MHz): δ 8.40 (s, 1H), 8.24 (d, J=8.3 Hz, 1H), 7.95 (d, J=7.9 Hz, 1H), 7.84 (t, J=7.1 Hz, 1H), 7.67 (t, J=7.5 Hz, 1H), 7.45 (s, 1H), 5.74 (d, J=17.0 Hz, 1H), 5.44 (d, J=17.0 Hz, 1H), 5.30 (s, 2H), 2.15-2.41 (m, 2H), 2.12 (s, 3H), 1.95 (s, 3H), 1.65 (t, J=7.5 Hz, 3H). $^{13}C$ NMR ($CDCl_3$, 75 MHz): δ 170.3, 167.0, 157.4, 152.4, 149.0, 146.5, 145.5, 131.0, 130.5, 130.0, 128.4, 128.2, 128.1, 128.0, 120.0, 96.0, 76.8, 67.1, 54.7, 50.0, 31.7, 30.5, 30.4, 7.7. HRMS-FAB (m/z): $[M+H]^+$ calculated for $C_{24}H_{22}O_5N_2Br$: 497.0712, found: 497.0669.

Synthesis of Initiator 3. CPT (1 g, 2.87 mmol) and 1 g of Boc-protected glycine (5.74 mmol) were added into 50 mL of dry DCM. After the suspension was cooled to 0° C., DMAP (0.7 g, 5.74 mmol) and EDC.HCl (1.1 g, 5.74 mmol) were added to the suspension. The reaction mixture was stirred at 0° C. for 20 min then room temperature for 1 h. After washing with 1 N HCl (100 mL×3), 1% $NaHCO_3$ (100 mL×3), and brine (100 mL×1), the organic phase was dried over $MgSO_4$. Evaporation of the solvent under reduced pressure gave compound CPT-Gly-Boc (1.23 g, 86% yield), which is used in the next step without further purification. $^1H$ NMR ($CDCl_3$, 300 MHz): δ 8.42 (s, 1H), 8.26 (d, J=7.6 Hz, 1H), 7.96 (d, J=7.5 Hz, 1H), 7.86 (t, J=7.5 Hz, 1H), 7.69 (t, J=7.5 Hz, 1H), 7.30 (s, 1H), 5.71 (d, J=17.5 Hz, 1H), 5.42 (d, J=17.5 Hz, 1H), 5.31 (s, 2H), 4.99 (b, 1H), 4.14 (m, 2H), 2.13-2.38 (m, 2H), 1.42 (s, 9H), 1.00 (t, J=6.9 Hz 3H).

To a solution of compound CPT-Gly-Boc (1.3 g, 2.57 mmol) in 30 mL of DCM was added 4 mL of TFA. The reaction mixture was stirred at room temperature for 1 h. and then the solvent was removed under vacuum. The product was precipitated out in ethyl ether, filtered and dried under vacuum to give compound CPT-Gly (1.2 g, 90% yield). $^1H$ NMR (DMSO, 300 MHz): 8.74 (s, 1H), 8.37 (b, 3H), 8.16 (d, J=8.2 Hz, 2H), 7.89 (t, J=7.6 Hz, 1H), 7.74 (t, J=7.6 Hz, 1H), 7.30 (s, 1H), 5.56 (s, 2H), 5.34 (s, 2H), 4.36 (d, J=18.0 Hz, 1H), 4.11 (d, J=18.0 Hz, 1H), 2.19 (m, 2H), 0.96 (t, J=7.4 Hz, 3H). $^{13}C$ NMR (DMSO, 75 MHz): δ 167.4, 167.3, 156.9, 152.8, 148.3, 146.5, 145.1, 132.2, 131.0, 130.3, 129.2, 129.1 128.5 128.3, 119.35, 96.0, 77.9, 66.8, 50.7, 40.2, 30.6, 8.0. HRMS-FAB (m/z): $[M+H]^+$ calculated for $C_{22}H_{20}O_5N_3$: 406.1403, found: 406.1401.

To a solution of compound CPT-Gly (280 mg, 0.69 mmol) and DIPEA (267 mg, 2.07 mmol) in 10 mL DCM was added dropwise 2-bromoisobutyryl bromide (318 mg, 1.38 mmol) in 5 mL of DCM at −20° C. The reaction mixture was stirred at −20° C. for 20 min and then room temperature for 2 h. After washing with 1 N HCl (30 mL×3), 1% $NaHCO_3$ (30 mL×3), and brine (30 mL×1), the organic phase was dried over $MgSO_4$. After removing the $MgSO_4$ by filtration, evaporation of the solvent under reduced pressure gave crude product as a yellow solid, which is recrystallized from MeOH/CH$_2$Cl$_2$ (95:5) to give initiator 3 (135 mg, 35% yield) as light yellow solid. $^1$H NMR (CDCl$_3$, 300 MHz): δ 8.42 (s, 1H), 8.25 (d, J=8.6 Hz, 1H), 7.90 (d, J=8.1 Hz, 1H), 7.86 (t, J=7.5 Hz, 1H), 7.69 (t, J=7.5 Hz, 1H), 7.15 (s, 1H), 5.72 (d, 17.3 Hz, 1H), 5.42 (d, J=17.3 Hz, 1H), 5.30 (s, 2H), 4.20-4.40 (m, 2H), 2.13-2.39 (m, 2H), 1.97 (s, 3H), 1.92 (s, 3H), 1.01 (t, J=7.4 Hz, 3H). $^{13}$C NMR (CDCl$_3$, 75 MHz): δ 172.2, 168.7, 167.1, 157.3, 152.2, 148.9, 146.6, 145.2, 131.2, 130.8, 129.7, 128.4, 128.2, 128.1, 120.1, 96.0, 87.2, 77.2, 67.2, 61.6, 50.0, 42.1, 32.4, 32.3, 31.9, 7.6. HRMS-FAB (m/z): [M+H]$^+$ calculated for C$_{26}$H$_{24}$O$_6$N$_3$Br: 554.0927, found: 554.0927.

General Procedure for ATRP of MPC from CPT-initiators. CPT-initiator (29.0 mg, 0.06 mmol) was charged into a 10 mL two-neck round-bottom flask and three cycles of vacuum-nitrogen were employed. Nitrogen gas bubbled DMSO (1.5 mL) was injected with a syringe. After the initiator was completely dissolved, CuBr (8.6 mg, 0.06 mmol) and bipyridine (18.7 mg, 0.12 mmol) were added quickly under nitrogen atmosphere. Different amount of MPC dissolved in MeOH (0.5 mL) was then added to the mixture. The reaction mixture was then subjected to four freeze-pump-thaw cycles. The reaction mixture was stirred at room temperature and the polymerization conversion was monitored by NMR. The polymerization was stopped by precipitating the reaction mixture into THF (100 mL) and the crude product was isolated by filtration. The polymer was purified on silica column with MeOH—CH$_2$Cl$_2$ (95:5) as eluent to give polymer as light yellow solid. The polymers were characterized using $^1$H NMR and aqueous GPC.

Synthesis of CPT-PolyMPC Conjugates

Synthesis of Compound 5.

Chromium trioxide (25 g, 164 mmol) was dissolved into 300 mL of 1.5 M H$_2$SO$_4$ and the solution was cooled to 0° C. Compound 2-[2-(2-chloroethoxy)ethoxy]ethanol (8.3 g, 49 mmol) in 150 mL acetone was added into the Jones reagent dropwise and the reaction mixture was stirred at room temperature for 6 h. The acetone was removed by evaporation under vacuum and the aqueous phase was extracted with DCM (3×100 mL). After the combined organic phase was dried over MgSO$_4$, the 2-[2-(2-chloroethoxy)ethoxy]acetic acid (6.3 g, 70% yield) was obtained by removed the solvent by rotary evaporation. IR: (cm$^{-1}$) 1734 (C═O). $^1$H NMR (CDCl$_3$, 300 MHz): δ 10.49 (b, 1H), 4.23 (s, 2H), 3.80 (t, J=5.8 Hz, 4H), 3.74 (t, J=5.7 Hz, 2H), 3.66 (t, J=5.8 Hz, 2H). $^{13}$C NMR (CDCl$_3$, 75 MHz): δ 174.4, 71.4, 71.1, 70.4, 68.5, 42.6.

2-[2-(2-chloroethoxy)ethoxy]acetic acid (6.3 g, 34.4 mmol) and NaN$_3$ (9 g, 138 mmol) were dissolved in 20 mL of water. The reaction mixture was refluxed at 80° C. for 48 h. After cooling to room temperature, the reaction mixture was acidified with HCl solution and extracted with DCM (4×50 mL). The combined organic phase was dried over MgSO$_4$ and then MgSO$_4$ was removed by filtration. Solvent was removed under reduced pressure to obtain compound 5 as clear oil (5.0 g, 77% yield). IR: (cm$^{-1}$) 2097 (N═N═N). $^1$H NMR (CDCl$_3$, 300 MHz): δ 10.80 (b, 1H), 4.22 (s, 2H), 3.79 (t, J=5.7 Hz, 2H), 3.69-3.74 (m, 4H), 3.43 (t, J=5.3 Hz, 2H). $^{13}$C NMR (CDCl$_3$, 75 MHz): δ 174.7, 71.2, 70.5, 70.1, 68.4, 50.6. HRMS-FAB (m/z): [M+H]$^+$ calculated for C$_6$H$_{12}$O$_4$N$_3$: 190.0828, found: 190.0816.

Synthesis of Compound 6.

The compound 4 was synthesized according to the literature. 6-bromohexanoic acid (5 g, 25.6 mmol) was reacted with sodium azide (8.4 g, 129 mmol) in 50 mL of DMSO at room temperature to generate compound 4,6-azidohexanoic acid, which then was reacted with CPT using EDC/DMAP as coupling agents in DCM to obtain compound 6. IR: (cm$^{-1}$) 2094 (N═N═N). $^1$H NMR (CDCl$_3$, 300 MHz): δ 8.43 (s, 1H), 8.24 (d, J=8.3 Hz, 1H), 7.97 (d, J=8.0 Hz, 1H), 7.87 (t, J=7.0 Hz, 1H), 7.70 (t, J=7.1 Hz, 1H), 7.23 (s, 1H), 5.71 (d, J=17.6 Hz, 1H), 5.43 (d, J=17.6 Hz, 1H), 5.31 (s, 2H), 3.25 (t, J=6.8 Hz, 2H), 2.45-2.63 (m, 2H), 2.11-2.37 (m, 2H), 1.71 (qp, J=7.6 Hz, 2H), 1.63 (m, 2H), 1.42 (m, 2H), 1.00 (t, J=7.3 Hz, 3H).

Synthesis of Compound 7.

Compound 5 (327 mg, 1.72 mmol) and EDC hydrochloride (330 mg, 1.72 mmol) were dissolved in 20 mL DCM at 0° C. CPT (300 mg, 0.86 mmol) and DMAP (210 mg, 1.72 mmol) were added. The reaction was stirred at room temperature till the suspension turned clear. After washing with 1 N HCl (50 mL×3), 1% NaHCO$_3$ (50 mL×3), and brine (50 mL×1), the organic phase was dried over MgSO$_4$. After filtration, the solvent was removed by evaporation to gave a yellow solid, which is recrystallized from MeOH/CH$_2$Cl$_2$ (95:5) to give pure compound 7 (389 mg, 87% yield) as light yellow solid. IR: (cm$^{-1}$) 2104 (N═N═N). $^1$H NMR (CDCl$_3$, 300 MHz): δ 8.43 (s, 1H), 8.24 (d, J=8.0 Hz, 1H), 7.97 (d, J=8.0 Hz, 1H), 7.87 (t, J=7.5 Hz, 1H), 7.70 (t, J=7.5 Hz, 1H), 7.23 (s, 1H), 5.73 (d, J=17.4 Hz, 1H), 5.44 (d, J=17.4 Hz, 1H), 5.31 (s, 2H), 4.39 (d, J=5.0 Hz, 2H), 3.77 (t, J=5.5 Hz, 2H), 3.66-3.70 (m, 4H), 3.40 (t, J=5.1 Hz, 2H), 2.13-2.39 (m, 2H), 1.00 (t, J=7.4 Hz, 3H). $^{13}$C NMR (CDCl$_3$, 75 MHz): δ 169.7, 167.3, 157.3, 152.2, 148.9, 146.4, 145.4, 131.2, 130.7, 129.6, 128.4, 128.2, 128.2, 128.1, 120.3, 95.9, 76.4, 71.1, 70.6, 70.0, 68.2, 67.2, 50.6, 50.0, 31.8, 7.6. HRMS-FAB (m/z): [M+H]$^+$ calculated for C$_{26}$H$_{26}$O$_7$N$_5$: 520.1832, found: 520.1821.

Synthesis of Compound 8.

Compound 5 (304 mg, 1.60 mmol) and EDC hydrochloride (461 mg, 2.40 mmol) were dissolved in 20 mL DCM at 0° C. CPT-Gly TFA salt (415 mg, 0.80 mmol) and DMAP (293 mg, 2.40 mmol) were added. The reaction was stirred at room temperature for 5 h and then washed with 1 N HCl (30 mL×3), 1% NaHCO$_3$ (30 mL×3), and brine (30 mL×1), the organic phase was dried over MgSO$_4$. After filtration, the solvent was removed by rotary evaporation to give crud product, which is recrystallized from MeOH to give pure compound 8 (374 mg, 81% yield). IR: (cm$^{-1}$) 2113 (N═N═N). $^1$H NMR (CDCl$_3$, 300 MHz): δ 8.41 (s, 1H), 8.26 (d, J=8.5 Hz, 1H), 7.95 (d, J=7.7 Hz, 1H), 7.85 (t, J=7.0 Hz, 1H), 7.68 (t, J=7.7 Hz, 1H), 7.37 (t, J=5.3 Hz, 1H), 7.27 (s, 1H), 5.71 (d, J=17.2 Hz, 1H), 5.43 (d, J=17.2 Hz, 1H), 5.29 (s, 2H), 4.46-4.54 (dd, J$_1$=18.6 Hz, J$_2$=6.5 Hz, 1H), 4.18-4.26 (dd, J=18.6 Hz, J$_2$=4.7 Hz, 1H), 4.02 (q, J=8.2 Hz, 1H), 3.66-3.70 (m, 2H), 3.62 (t, J=5.0 Hz, 4H), 3.34 (t, J=4.9 Hz, 2H), 2.14-2.40 (m, 2H), 1.00 (t, J=7.5 Hz, 3H). $^{13}$C NMR (CDCl$_3$, 75 MHz): δ 170.3, 169.0, 167.1, 157.3, 152.2, 148.9, 146.6, 145.3, 131.2, 130.7, 129.8, 128.4, 128.2 (2C overlap), 182.1, 120.2, 96.0, 76.9, 71.1, 70.3, 70.2, 70.0, 67.2, 50.6, 50.0, 40.4, 31.9, 7.6. HRMS-FAB (m/z): [M+H]$^+$ calculated for C$_{28}$H$_{29}$N$_6$O$_8$: 577.2047, found: 577.2021.

Synthesis of TMS-PgMA. The TMS protected alkyne monomer was synthesized according to the literature. 3-(Trimethylsilyl)propargyl alcohol (2 g, 15.6 mmol) and triethylamine (2 g, 20.3 mmol) in 20 mL of dry ethyl ether was cooled to −20° C. A solution of methacryloyl chloride (2 g, 18.7 mmol) in 10 mL of dry ethyl ether was added dropwise over 30 min. The reaction mixture was stirred for 30 min at −20° C., then overnight at room temperature. The precipitation was removed by filtration and the solvent was removed by rotary evaporation. The crude product was further purified on silica column chromatography eluted with hexane-ethyl ether (100:1) to give the pure TMS-PgMA monomer as clear oil (4.0 g, 58% yield). IR: (cm$^{-1}$) 2961 (C—H), 1723 (C=O), 1638 (C=C). $^1$H NMR (CDCl$_3$, 300 MHz): δ 6.16 (m, 1H), 5.61 (m, 1H), 4.75 (s, 2H), 1.95 (m, 3H), 0.18 (s, 9H). $^{13}$C NMR (CDCl$_3$, 75 MHz): δ 166.6, 135.7, 126.4, 99.1, 91.9, 53.0, 18.3, 0.3. HRMS-FAB (m/z): [M]$^+$ calculated for C$_{10}$H$_{16}$O$_2$Si: 196.0920, found: 196.0891.

TABLE 8

$M_n$ and PDI values of CPT-polyMPC conjugates before and after CPTs were cleaved from polymer

| Polymer | Before hydrolysis | | After hydrolysis | | | |
|---|---|---|---|---|---|---|
| | $M_n$ (kg/mol) | PDI | $M_n'$ (kg/mol) | PDI' | $M_n'/M_n$ | PDI'/PDI |
| CP1 | 5.2 | 1.27 | 6.8 | 1.17 | 1.31 | 0.92 |
| CP2 | 5.5 | 1.25 | 7.5 | 1.16 | 1.36 | 0.93 |
| CP3 | 5.1 | 1.36 | 7.5 | 1.17 | 1.47 | 0.86 |
| CP4 | 13.5 | 1.41 | 15.0 | 1.28 | 1.11 | 0.91 |
| CP5 | 7.0 | 1.26 | 9.0 | 1.16 | 1.29 | 0.92 |

General Procedure for One-Pot of ATRP and Click Chemistry.

CPT azide compound was charged into a 10 mL two-neck round-bottom flask and three cycles of vacuum-nitrogen were employed. Nitrogen gas bubbled DMSO (2 mL) was injected with a syringe. After the CPT azide was completely dissolved, a solution of ethyl 2-bromoisobutyrate (11.7 mg. 0.06 mmol), MPC and alkyne monomer in 0.7 mL methanol was injected. CuBr (17 mg, 0.12 mmol) and bipyridine (37.4 mg, 0.24 mmol) were added quickly under nitrogen atmosphere. The reaction mixture was then subjected to four freeze-pump-thaw cycles. The reaction mixture was stirred at room temperature for 20 h and the polymerization conversion was monitored by $^1$H NMR. The polymerization was stopped by precipitating the reaction mixture into THF (100 mL) and the crude product was isolated by filtration. The crude product was further purified on silica column with MeOH—CH$_2$Cl$_2$ (95:5) as eluent to give the CPT-polyMPC conjugates as light yellow solid. The polymers were characterized using NMR and aqueous GPC.

TEM.

TEM images were obtained using a JEOL 2000FX transmission electron microscope operating at an acceleration voltage of 200 kV. The samples were prepared by dropping 2 μL of polymer solution onto the carbon-coated copper grid. After the samples were dried, 1 wt % phosphotungstenic acid solution (PTA) was used to stain the samples.

DLS Measurement.

DLS was performed on a Malvern Zetasizer Nano-ZS (4 mW He—Ne laser, 633 nm) with a detector set to collect back-scattered light 173 degree angle. The light scattering intensity was recorded with fixed measurement position and attenuator for different concentrations. The size measurements were performed at polymer concentration of 1 mg/mL, and optimum position and automatic attenuation selection were chosen to generate the optimum correlation curve. Samples was dissolved in water and filtered through 0.45 μm filter membrane one day before the measurement. Each measurement was performed at 25° C. by equilibrating the samples for 10 min.

Calibration of CPT Loading in Polymer.

Compounds 6, 7, and 8 were dissolved in DMSO-MeOH (1:1) at concentration of 0.01 mg/mL and copolymers (CP1-5) were also dissolved in DMSO-MeOH (1:1) at concentration of 0.1 mg/mL. The CPT loading in each polymer was calculated based on UV absorbance values at 370 nm and known concentration of its corresponding CPT azide compound.

Drug Release Study

The CPT containing polymers were dissolved into different media at a concentration of 3 mg/mL. The mixtures were incubated at 37° C. and aliquots (100 μL) were taken out at different time points. Twenty μL of the sample from PBS and cell culture media were analyzed by SEC-HPLC. The sample taken from mouse serum and human plasma were mixed with 200 uL of PBS and filtered through 0.45 μm filter membrane; 60 μL of the filtrate was analyzed by SEC-HPLC. The stability profile was generated by plotting the percentage of remaining CPT on the polymer over a time course. The percentage was calculated based on the peak area of UV absorbance at 370 nm. The sample was also analyzed by reverse phase HPLC, and evaluation of the integrity of the released CPT was based on the retention times.

Cell Culture

The COLO 205 and OVCAR 3 cancer cells were cultured in RPMI-1640 medium supplemented with 10% fetal bovine serum (FBS) or 20% FBS and 0.01 mg/ml bovine insulin, while MCF 7 cells were cultured in MEM medium supplemented with 10% FBS and 0.01 mg/ml bovine insulin. All cells were grown in 5% CO$_2$ incubators at 37° C. For in vitro cytotoxicity assays cells were seeded into 96 well plates and after reaching about 40% cell density were incubated for 72-96 hours with varying camptothecin equivalent concentrations of polymer drug conjugates as well as polymer control (i.e., without drug attachment). Cell viability post-treatment was measured using CellTiter-Glo luminescent cell viability assays (Promega) as per manufacturer's instructions on a FLUOstar OPTIMA plate reader (BMG LABTECH). The percentage camptothecin mediated toxicity was calculated with respect to untreated cells, and graphed to give dose response curves. IC$_{50}$ values for each treatment were then calculated using the GraphPad Prism4 statistical analysis software.

Synthesis of Azide Containing PolyMPC

Synthesis of Compound 10

Sodium azide (7.8 g, 120 mmol) and 2-[2-(2-chloroethoxy)ethoxy]ethanol (5.1 g, 30 mmol) were dissolved in 15 mL of water, and sodium iodide was added as catalyst. The reaction mixture was heated to 60° C. for 72 h. After extraction with 4×50 mL DCM, the combined organic phase was dried over MgSO$_4$. The solvent was removed by rotary evaporation under reduced temperature and the residue was further dried under vacuum to give compound 10 as clear oil (4.5 g, 86% yield). IR: (cm$^{-1}$) 2097 (N=N=N). $^1$H NMR (CDCl$_3$, 300 MHz): δ 3.74 (t, J=4.9 Hz, 2H), 3.68 (m, 6H), 3.61 (t, J=4.6 Hz, 2H), 3.40 (t, J=5.0 Hz, 2H), 2.54 (b, 1H). $^{13}$C NMR (CDCl$_3$, 75 MHz): δ 72.5, 70.6, 70.4, 70.0, 61.7, 50.6.

Synthesis of Compound 12

A solution of compound 10 (4.4 g, 25 mmol) and triethylamine (5.5 g, 50 mmol) in 40 mL of dry ethyl ether was stirred at −20° C. Methylacryloyl chloride (5.35 g, 50 mmol) in 20 mL of dry ethyl ether was added in dropwise. The reaction mixture was kept at −20° C. for 1 hour followed room temperature overnight. The salt was removed by filtration and the filtrated was concentrated with rotary evaporation under reduced temperature. The residue was further purified by silica-gel column chromatography using gradient hexane-ethyl ether (10:1 to 1:1) as eluent to give pure compound 12 as clear oil (3.5 g, 57% yield). IR: (cm$^{-1}$) 2097 (N=N=N). $^1$H NMR (CDCl$_3$, 300 MHz): δ 6.15 (s, 1H), 5.59 (t, J=1.4 Hz, 1H), 4.32 (t, J=4.8 Hz, 2H), 3.77 (t, J=4.9 Hz, 2H), 3.69 (m, 6H), 3.40 (t, J=4.9 Hz, 2H), 1.97 (s, 3H). $^{13}$C NMR (CDCl$_3$, 75 MHz): δ 167.4, 136.2, 125.8, 70.7 (overlap), 70.1, 69.2, 63.9, 50.7, 18.3. HRMS-FAB (m/z): [M+H]$^+$ calculated for $C_{10}H_{18}O_4N_3$: 244.1297, found: 244.1291.

Synthesis of Copolymer CP6

EBiB (11.7 mg, 0.06 mmol), MPC (530 mg, 1.8 mmol), and compound 12 (146 mg, 0.6 mmol) were charged into a 10 mL two-neck round-bottom flask and three cycles of vacuum-nitrogen were employed. Degassed MeOH (2 mL) was injected with a degassed syringe. CuBr (8.5 mg, 0.06 mmol) and bipyridine (18.8 mg, 0.12 mmol) were added quickly under nitrogen atmosphere. The reaction mixture was then subjected to three freeze-pump-thaw cycles. The reaction mixture was stirred at room temperature for 20 h with 88% conversion by $^1$H NMR. The polymerization was stopped by opening to air and the crude product was further purified by chromatography on silica-gel to give the copolymer CP6 as white solid (426 mg, 62% yield). The polymers were characterized with FT-IR, NMR and aqueous GPC.

Synthesis of Compound 14

CPT-Gly TFA salt (207 mg, 0.4 mmol) was added to a solution of 4-pentynoic acid (78 mg, 0.8 mmol) and DMAP (147 mg, 1.2 mmol) in 20 mL of dry DCM. The suspension was cooled to 0° C. and EDC hydrochloride (208 mg, 1.2 mmol) was added as solid. The reaction mixture was stirred at 0° C. for another 30 min and then room temperature overnight. The final clear brown solution was washed with 1% NaHCO$_3$ (20 mL×3), 1 N HCl (20 mL×3), and brine (20 mL×1), the organic phase was dried over MgSO$_4$. After filtration, the solvent was removed by evaporation to gave a yellow solid, which is recrystallized from MeOH/CH$_2$Cl$_2$ (95:5) to give pure compound 14 (140 mg, 74% yield) as yellow solid. $^1$H NMR (DMSO, 300 MHz): δ 8.69 (s, 1H), 8.51 (t, J=5.6 Hz, 1H), 8.19 (d, J=8.5 Hz, 1H), 8.13 (d, J=8.2 Hz, 1H), 7.88 (t, J=7.1 Hz, 1H), 7.72 (d, J=7.3 Hz, 1H), 7.16 (s, 1H), 5.50 (s, 2H), 5.28 (s, 2H), 3.99-4.25 (m, 2H), 2.77 (s, 1H), 2.37 (m, 4H), 2.17 (q, J=7.3 Hz, 2H), 0.92 (t, J=7.2 Hz, 3H). $^{13}$C NMR (DMSO, 75 MHz): δ 171.3, 169.5, 167.5, 156.9, 152.8, 148.3, 146.4, 145.5, 132.0, 130.9, 130.2, 129.4, 129.0, 128.4, 128.2, 119.4, 95.7, 84.1, 76.7, 71.9, 66.8, 50.7, 34.3, 30.8, 14.5, 8.0. HRMS-FAB (m/z): [M+H]$^+$ calculated for $C_{27}H_{24}O_6N_3$: 486.1665, found: 486.1674.

Synthesis of Conjugate CP7

Copolymer CP6 (200 mg) and compound 14 (43 mg, 0.09 mmol) was stirred in degassed MeOH (0.5 mL) and DMSO (1.5 mL). CuBr (12.8 mg, 0.09 mmol) and bipyridine (28.1 mg, 0.18 mmol) were added quickly under nitrogen atmosphere. The reaction mixture was then subjected to three freeze-pump-thaw cycles. After 22 h, the reaction suspension turned to clear solution and the reaction mixture was stirred at room temperature for another 26 h. The crude product was obtained by precipitation into dry THF, followed by filtration. Further purification of crude product on silica-gel column gave pure conjugate CP7 as brown solid (121 mg, 50% yield). The conjugate was characterized with $^1$H NMR, FT-IR and GPC. UV calibration of CPT loading in the polymer was performed in the same manner as described.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance which can be adapted to the practice of this invention in its various embodiments and equivalents thereof.

What is claimed is:

1. A co-polymer comprising the structure of:

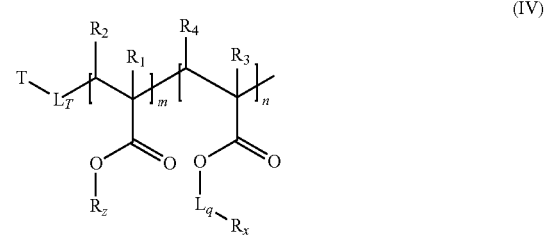

wherein
each of $R_1$ and $R_3$ is independently a hydrogen, alkyl, or halogen;
each of $R_2$ and $R_4$ is independently a hydrogen, ($C_1$-$C_{15}$) alkyl, ($C_1$-$C_{15}$) alkyloxy, or halogen;
$R_Z$ is a group comprising a zwitterionic moiety;
m is an integer from 1 to about 500;
n is an integer from 1 to about 100;
$L_q$ is a linking group;
$R_X$ is a group comprising an azide or a carbon-carbon triple bond;
$L_T$ is a linking group;
T is a targeting moiety towards a biological target; and
wherein T is selected from the group consisting of an antibody, protein, aptamer, or a small molecule comprising a folate moiety.

2. The co-polymer of claim 1, wherein, $L_T$ comprises an amide moiety.

3. The co-polymer of claim 1, wherein the co-polymer has a $M_n$ from about 5 kDa to about 100 kDa.

4. The polymer of claim 1, wherein the polymer is crosslinked.

5. The polymer of claim 1, wherein the polymer is a block-copolymer.

* * * * *